United States Patent [19]
Wilcox et al.

[11] Patent Number: 5,722,829
[45] Date of Patent: Mar. 3, 1998

[54] CARTRIDGE DISPENSING SYSTEM FOR DENTAL MATERIAL

[75] Inventors: Malcolm W. Wilcox, Woodbury; James E. Nash, St. Paul; Thomas W. Martin, Maplewood; Alex Rodriguez, Jr.; Ralph F. Rogers, both of Woodbury, all of Minn.

[73] Assignee: Minnesota Mining & Manufacturing Co., St. Paul, Minn.

[21] Appl. No.: 547,451

[22] Filed: Oct. 24, 1995

Related U.S. Application Data

[63] Continuation-in-part of Ser. No. 394,724, Feb. 27, 1995, abandoned.

[51] Int. Cl.$^6$ ........................................ A61C 5/04
[52] U.S. Cl. ................. 433/90; 222/137; 222/145.1
[58] Field of Search ........................ 433/89, 90, 226, 433/116; 604/82, 173, 223, 224, 227, 232; 222/137, 145.1, 275, 326, 391

[56] References Cited

U.S. PATENT DOCUMENTS

| | | | |
|---|---|---|---|
| 3,806,097 | 4/1974 | Devellian et al. | 259/4 |
| 4,081,112 | 3/1978 | Chang | 222/391 |
| 4,084,320 | 4/1978 | Skeirik | 32/60 |
| 4,198,756 | 4/1980 | Dragan | 222/326 |
| 4,260,077 | 4/1981 | Schroeder | 222/137 |
| 4,340,367 | 7/1982 | Vadas et al. | 433/89 |
| 4,366,919 | 1/1983 | Anderson | 222/137 |
| 4,431,414 | 2/1984 | Lawrence | 433/90 |
| 4,471,888 | 9/1984 | Herb et al. | 222/137 |
| 4,472,141 | 9/1984 | Dragan | 433/90 |
| 4,479,781 | 10/1984 | Herold et al. | 433/90 |
| 4,538,920 | 9/1985 | Drake | 366/177 |
| 4,546,767 | 10/1985 | Smith | 128/92 E |
| 4,789,336 | 12/1988 | Lewis | 433/116 |
| 4,801,008 | 1/1989 | Rich | 206/219 |
| 4,913,553 | 4/1990 | Falco | 366/129 |
| 4,989,758 | 2/1991 | Keller | 222/137 |
| 4,993,948 | 2/1991 | Cameron et al. | 433/90 |
| 4,995,540 | 2/1991 | Colin et al. | 222/132 |
| 5,005,735 | 4/1991 | Keller | 222/137 |
| 5,052,927 | 10/1991 | Discko, Jr. | 433/90 |
| 5,064,098 | 11/1991 | Hutter, III et al. | 222/137 |
| 5,080,493 | 1/1992 | McKown et al. | 366/177 |
| 5,100,320 | 3/1992 | Martin et al. | 433/90 |
| 5,125,836 | 6/1992 | Dragan et al. | 433/90 |
| 5,129,825 | 7/1992 | Discko, Jr. | 222/134 |
| 5,137,181 | 8/1992 | Keller | 222/134 |
| 5,165,890 | 11/1992 | Discko, Jr. | 433/90 |
| 5,197,875 | 3/1993 | Nerli | 433/80 |
| 5,236,108 | 8/1993 | House | 222/541 |
| 5,306,147 | 4/1994 | Dragan et al. | 433/90 |
| 5,330,079 | 7/1994 | Keller | 222/135 |
| 5,333,760 | 8/1994 | Simmen | 222/137 |
| 5,336,014 | 8/1994 | Keller | 403/24 |
| 5,336,088 | 8/1994 | Discko, Jr. | 433/90 |
| 5,382,162 | 1/1995 | Sharp | 433/116 |

FOREIGN PATENT DOCUMENTS

| | | |
|---|---|---|
| 0 232 733 | 8/1987 | European Pat. Off. . |
| 319639 | 6/1989 | European Pat. Off. ............ 433/90 |
| 0 539 074 | 4/1993 | European Pat. Off. . |
| 0 563 749 | 10/1993 | European Pat. Off. . |
| 3903315 | 8/1989 | Germany . |
| 62-43634 | 3/1987 | Japan . |

*Primary Examiner*—Cary E. O'Connor
*Attorney, Agent, or Firm*—James D. Christoff

[57] ABSTRACT

A dispensing system for dental material made of two components has a dual chamber cartridge that releasably connects to an applicator. The chambers of the cartridge are located in an over-under orientation relative to the user's grip on the applicator, enabling the system to be especially useful for placing dental material in regions of the patient's oral cavity that are difficult to access. Certain embodiments of the invention include a static mixing assembly having a swivelable cannula, and an exit conduit of the mixing assembly is optionally curved along its length. Other aspects of the invention relate to a reusable hygienic sheath useful for covering a dual chamber cartridge as well as a single chamber cartridge.

46 Claims, 15 Drawing Sheets

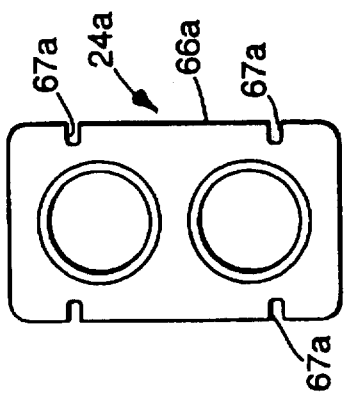
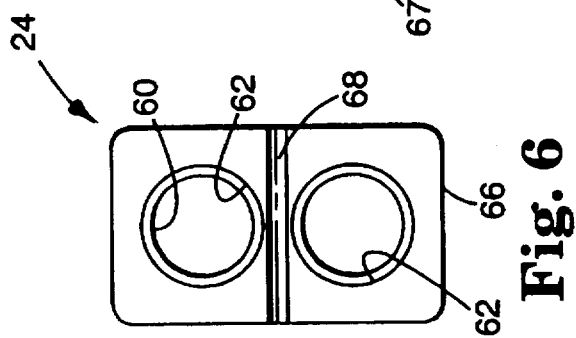
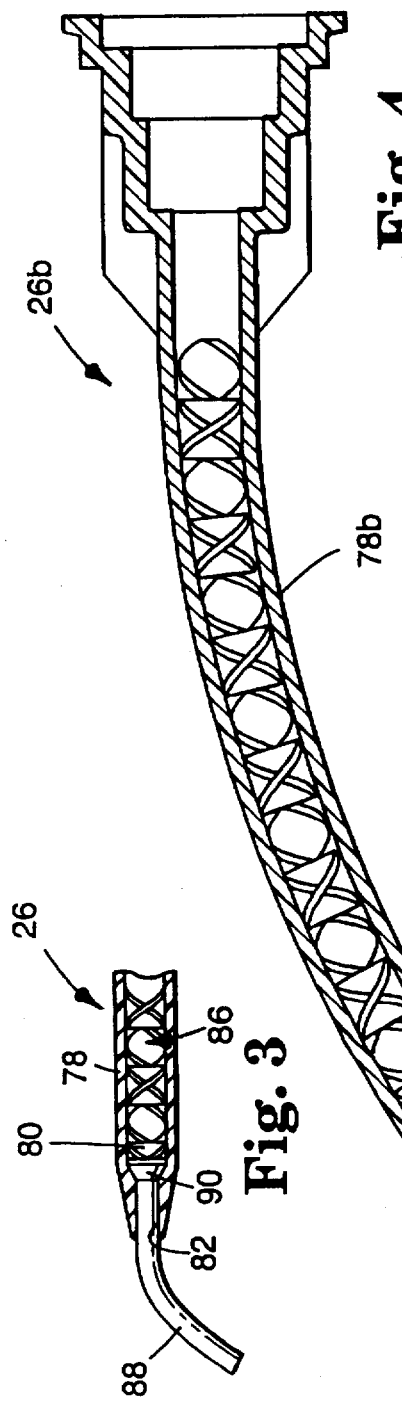
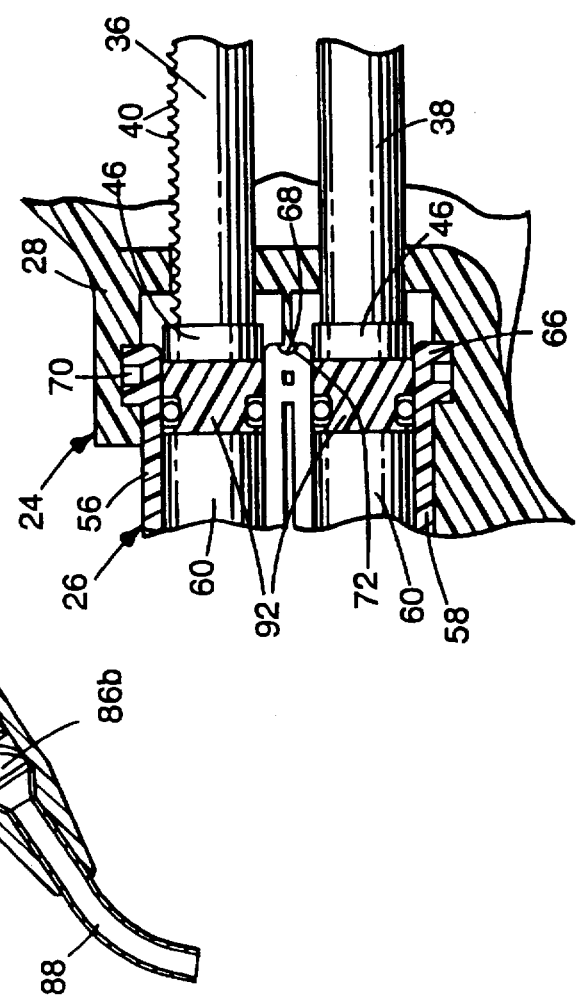

CARTRIDGE DISPENSING SYSTEM FOR DENTAL MATERIAL

This application is a continuation-in-part of U.S. Ser. No. 08/394,724 filed Feb. 27, 1995, now abandoned.

BACKGROUND OF THE INVENTION

1. Field of the Invention

This invention relates to a system for dispensing material used in dentistry.

2. Description of the Related Art

A variety of dispensing systems are used in the field of dentistry. Many dental dispensing systems include an applicator with plunger and a disposable cartridge that is detachably connected to the applicator. The plunger is movable toward a chamber of the cartridge in order to dispense dental material from the chamber. Once the chamber is empty, the cartridge is detached from the applicator and replaced with a new cartridge.

Dual chamber dispensing systems are widely used in dentistry for storing, mixing and dispensing impression material. Such dispensing systems are often called "double barrel syringes", and hold a catalyst component in one chamber and a base component in another chamber. A pair of linked-together plungers dispense portions of each impressioning component simultaneously such that measuring of the separate components is rendered unnecessary.

One example of a double barrel dispensing syringe is described in U.S. Pat. No. 4,538,920 which is assigned to assignee of the present invention. The syringe includes an exit conduit that has a plurality of helical static mixing elements. The components are thoroughly mixed during passage through the exit conduit, and mixing by hand can be avoided.

Dual chamber cartridge dispensing systems are typically used in the field of dentistry to deliver impression material to an impression tray before the tray is placed in the oral cavity. Occasionally, however, the dental practitioner may attempt to use the system to deliver the impressioning material directly into the oral cavity, as for example when an impression of only a single tooth is needed. Unfortunately, conventional dual chamber cartridge dispensing systems are somewhat bulky and it has been difficult to place the material in certain areas of the oral cavity, particularly in posterior areas where access is limited.

SUMMARY OF THE INVENTION

Recently, advances have been made in the field of dental restorative materials that are used to repair cavities in the teeth or restore damaged tooth structure. The advances include a glass ionomer restorative material such as is described in pending U.S. patent application Ser. No. 08/202,839, entitled "PASTE/PASTE GLASS IONOMER CEMENT SYSTEM AND METHODS", filed on Feb. 28, 1994 and assigned to the assignee of the present invention. The glass ionomer material described therein is made of two initially separate components that, if desired, can be mixed in a static mixer and then discharged directly to a selected location in the oral cavity.

The method of applying restorative material to tooth structure involves the use of relatively small quantities of material that should be placed as accurately as possible on the desired location. However, access to the cavity or damaged tooth structure can be especially difficult in some circumstances, such as when the cavity or damaged structure is in a posterior area or is in an interproximal area (i.e., in a location next to an adjacent tooth). The aforementioned double barrel syringe typically used for impression material is too large and cumbersome in many instances for satisfactory use with restorative material.

In accordance with the present invention, a dispensing system includes an applicator having a body, an elongated handle connected to the body and a pair of plungers movable relative to the body. A first container is connected to the body and has a chamber with a longitudinal axis. A second container is connected to the body and has a chamber with a longitudinal axis. The plungers are movable toward the chambers of the first container and the second container, and the axis of the first container and the second container generally lie in a common reference plane. The handle depends from the body in a direction generally parallel to the reference plane. The chambers of the first container and the second container each have a component of a dental material.

Another aspect of the present invention relates to a method of dispensing dental material made of a first component and a second component to a location in the oral cavity of a patient. The method comprises the steps of providing a first and second container each having an elongated chamber containing a component of a dental material, and connecting the first and second containers to a dispensing applicator having a depending handle. The method also includes the steps of holding the applicator in an orientation wherein the handle is generally parallel to the occlusal plane of the patient, and simultaneously orienting the longitudinal axes of the chambers of the first and second containers in a side-by-side, mesial and distal relationship to each other relative to mesial and distal directions in the patient's oral cavity as the first and second component are dispensed toward a location in the oral cavity.

The invention is also directed to an applicator for dispensing material from a cartridge having a first chamber and a second chamber in side-by-side relation to the first chamber. The applicator comprises a body, a handle depending from the body, and an arm located next to the handle and movable relative to the body. A first elongated plunger is movably connected to the body, and a second elongated plunger is coupled to the first plunger in side-by-side relation and is movably connected to the body. The arm when moved relative to the body is operable to move the first plunger and the second plunger in a forwardly direction relative to the body. A pivot connects the arm to the body, and the first plunger and the second plunger are located between the pivot and the arm.

Another aspect of the present invention concerns a dispensing system comprising an applicator having a body with a receptacle, a handle connected to the body and a pair of plungers movable relative to the body. The system also includes a cartridge having a first container, a second container and a flange connected to the first container and the second container. The first container and the second container each include a chamber containing one component of a material to be dispensed. The flange is detachably received in the receptacle for connecting the cartridge to the body. The plungers are movable in respective chambers to dispense the component in each chamber. One of the flange and the receptacle includes a recess, and the other of the flange and the receptacle includes a tab received in the recess when the flange is received in the receptacle.

The present invention also involves a dispensing cartridge comprising a first container having a chamber with a rear opening, a second container having a chamber with a rear opening, and a flange connected to the first container and the second container. The flange surrounds the rear opening of the first container and the second container. The flange includes an outer side and a rear end, and also includes at least one recess extending at least partially along the side and the end.

Another aspect of the present invention relates to a static mixing assembly comprising an exit conduit having an elongated cavity and a front opening, a static mixing element received in the cavity of the exit conduit, and a cannula extending outwardly from the front opening of the exit conduit. The cannula includes an outwardly flared rear section located in the cavity adjacent the front opening. The rear section is located between the front opening of the exit conduit and the static mixing element.

The invention also concerns a dispensing system comprising an applicator having a body with a receptacle and a plunger movably connected to the body. The system also includes a container that is removably received in the receptacle and has a chamber for containing a material to be dispensed. The plunger is movable toward the chamber in order to dispense material from the chamber. The system further includes a discharge tip for conveying material dispensed from the container toward an application site, and a coupling for connecting the discharge tip to the container. The coupling is shiftable between a locked orientation wherein the discharge tip is non-releasably connected to the container and an unlocked orientation wherein the discharge tip may be released from the container. A hygienic sheath removably extends over at least a portion of the container and the discharge tip. The sheath when extending over the container and the discharge tip retains the coupling in the locked orientation.

Another embodiment of the invention is directed toward a dispensing system that comprises an applicator having a body with a receptacle and a plunger movably connected to the body. A container is removably received in the receptacle and includes a chamber for containing a material to be dispensed. The plunger is movable toward the chamber in order to dispense material in the chamber. A discharge tip is detachably connected to the container for conveying material dispensed from the container toward an application site. The discharge tip includes a section being made of a material having a certain Young's modulus. A hygienic sheath extends over at least a portion of the container and the discharge tip. The sheath includes a portion that is in interference fit relation with the section of the discharge tip for releasably retaining the sheath in coupled relation to the discharge tip. The sheath portion is made of a relatively rigid material having a higher Young's modulus than the aforementioned certain Young's modulus of the material of the discharge tip section.

The present invention in its various aspects provides significant advantages over single component and two component dispensing systems known in the past. In certain embodiments, access to posterior regions of the oral cavity is greatly facilitated. Use of such embodiments is more comfortable for the patient in many instances, as the patient's jaws need not be opened as widely as might be necessary with prior art dual component dispensing systems. Other aspects and advantages will become apparent following a review of the drawings and a reading of the detailed description that follow.

BRIEF DESCRIPTION OF THE DRAWINGS

FIG. 3 is an enlarged, fragmentary, side cross-sectional view of a static mixing assembly of the system shown in FIGS. 1–2;

FIG. 4 is a view somewhat similar to FIG. 3 except in accordance with another embodiment of the invention;

FIG. 5 is an enlarged, fragmentary, side cross-sectional view of a coupling for connecting an applicator and the cartridge of the system shown in FIGS. 1–2;

FIG. 6 is an end elevational view of the flange alone that is shown in FIG. 5;

FIG. 7 is a view somewhat similar to FIG. 5 except in accordance with another embodiment of the invention;

DETAILED DESCRIPTION OF THE PREFERRED EMBODIMENTS

Figure 1:
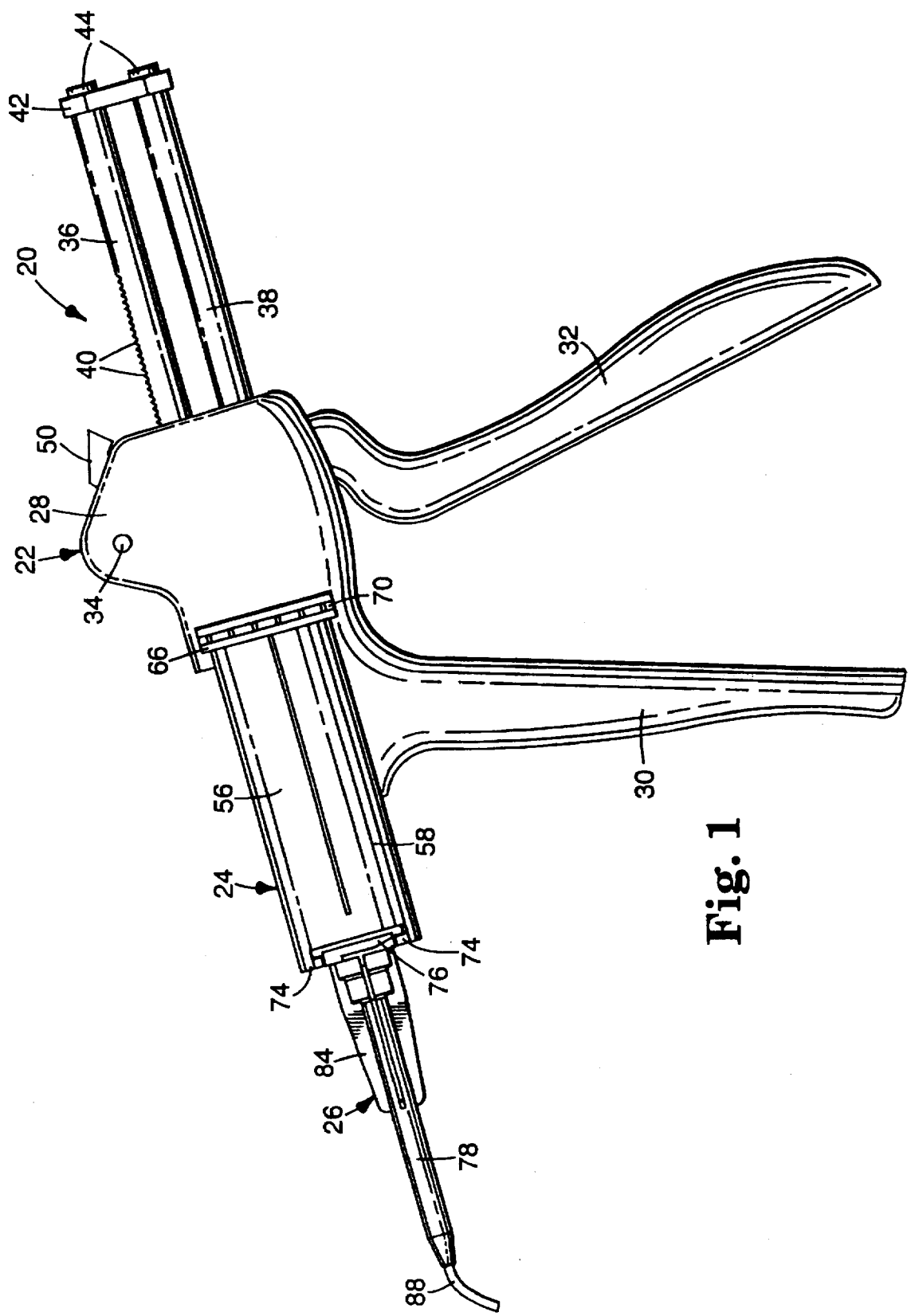
FIG. 1 is a side elevational view of a dispensing system according to one embodiment of the invention.
Figure 2:
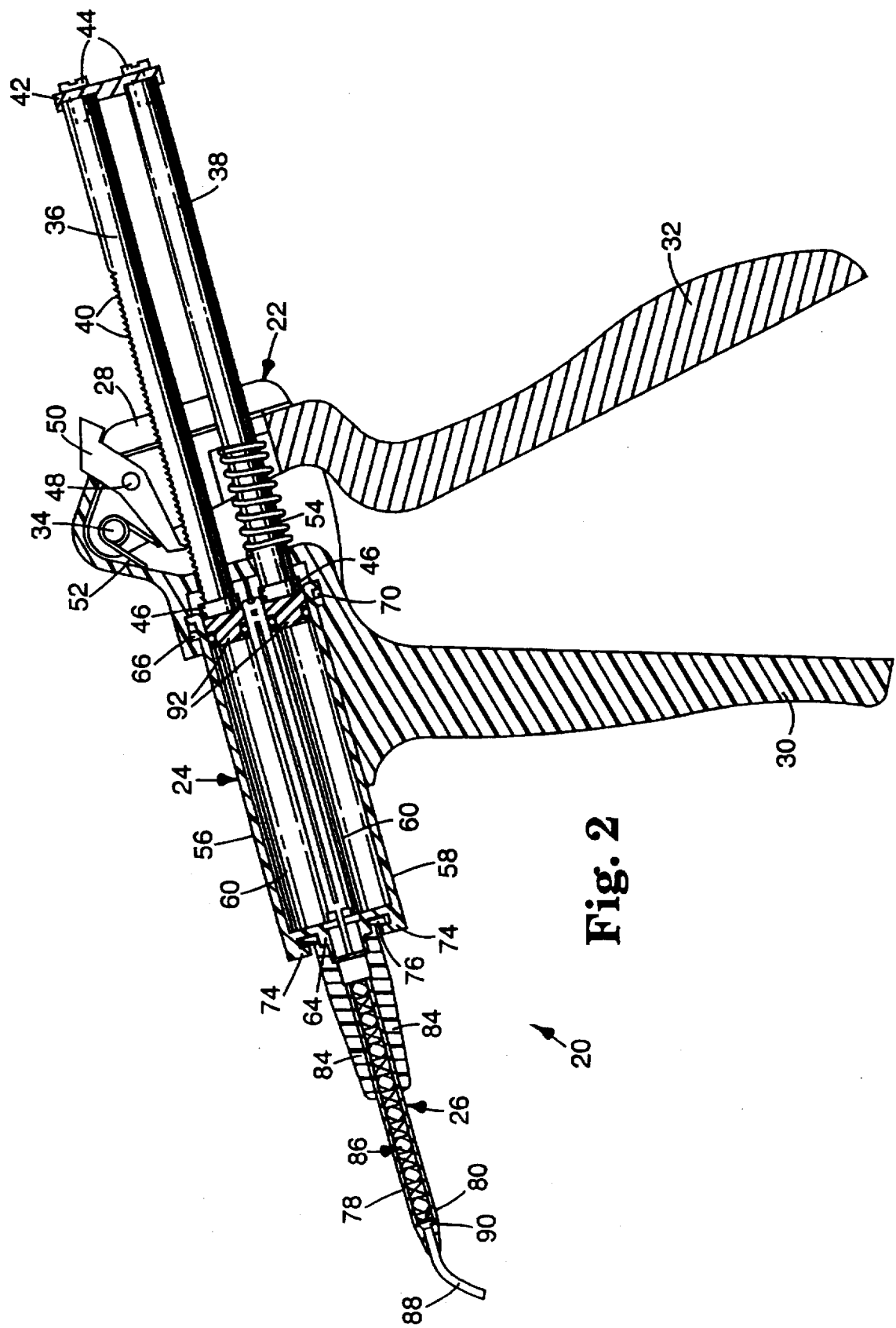
FIG. 2 is a side cross-sectional view of the system shown in FIG. 1.

An overall view of a dispensing system according to one embodiment of the invention is shown in FIGS. 1–2 and is designated by the numeral 20. The dispensing system 20 broadly includes an applicator 22, a dual chamber dispensing cartridge 24 detachably connected to the applicator 22 and a discharge tip such as a static mixing assembly 26 that is detachably connected to the front of the cartridge 24.

Turning initially to the applicator 22 in more detail, the applicator 22 includes a hollow body 28 and an elongated, depending handle 30 that is connected to the body 28. The body 28 and the handle 30 are each made in right and left half-sections that are substantially mirror-image of each other, and in each half-section the corresponding portion of the body 28 is integrally molded with the corresponding portion of the handle 30.

The applicator 22 also includes an arm 32 that depends from the body 28 and is located next to the handle 30. An upper portion of the arm 32 is bifurcated and extends within the hollow area of the body 28. A pivot 34, in the form of a cylindrical metal rod, extends transversely between right and left half-sections of the body 28, and pivotally connects the upper bifurcated portion of the arm 32 to the body 28 to thereby enable the arm 32 to move in swinging fashion relative to the handle 30.

The applicator 22 also includes a first elongated plunger 36 and a second elongated plunger 38 that is located below the first plunger 36 in 20 parallel, side-by-side relation. The handle 30 extends at an angle of preferably less than 90 degrees, and more preferably at an angle of about 75 degrees relative to the longitudinal axes of the plungers 36, 38. Both of the plungers 36, 38 have a smooth cylindrical outer surface, except that the top plunger 36 has a top surface with a series of flat teeth 40 that extend along a major extent of the length of the first plunger 36.

The plungers 36, 38 are secured together for simultaneous movement by a rigid block 42 that is connected to the rear end of the plungers 36, 38 by screws 44. The front end of each plunger 36, 38 includes a slightly enlarged cylindrical head 46 (FIG. 2) that is optionally connected to the corresponding plunger 36, 38 by a longitudinally extending screw (not shown in the drawings).

The plungers 36, 38 pass through two respective holes located in a rear wall of the body 28 and also two respective holes located in an interior wall of the body 28 immediately behind the position of the heads 46 that is illustrated in FIG. 2. The enlarged heads 46, being larger than the adjacent holes in the body 28, prevent the plungers 36, 38 from detaching from the body 28 when the plungers 36, 38 are pulled in a rearward direction. Alternatively, the heads 46 could be eliminated, or be made equal in diameter to the plungers 36, 38 so that the latter could be removed from the body 28 if desired.

A second pivot 48, also in the form of a cylindrical metal rod, extends between the bifurcated sections of the upper portion of the arm 32 immediately behind and somewhat below the pivot 34 as shown in FIG. 2. The pivot 48 passes through a hole in a pawl 50 that extends through the space between the bifurcated upper portion of the arm 32. A coil spring 52 is wrapped around the pivot 34 and has an upper leg that bears upwardly against an upper wall of the body 28 and a lower leg that bears downwardly against a forward section of the pawl 50. The spring 52 urges a chisel-shaped lower front edge of the pawl 50 into releasable engagement with one of the teeth 40 of the upper plunger 36.

A coiled compression spring 54 is also located in the hollow area of the body 28. Advantageously, the spring 54 is received around a portion of the lower plunger 38 in order to save space and obviate the need for additional connecting members or the like. The front end of the spring 54 bears against the inner wall of the body 28, while the rear end of the spring 54 bears against a rear end of a slightly enlarged channel constructed in the opposing sections of the upper bifurcated portion of the arm 32 next to the lower plunger 38. The spring 54 urges the arm 32 in a rearward direction and away from the handle 30.

To advance the plungers 36, 38, the arm 32 is swung about pivot 34. As the arm 32 moves toward the handle 30, engagement of the chisel-shaped lower front edge of the pawl 50 with the teeth 40 causes the plungers 36, 38 to simultaneously advance. Upon release of the arm 32, the spring 54 urges the arm 32 to move in a rearwardly direction away from the handle 30; however, frictional engagement of the plungers 36, 38 with the two pairs of holes in the body 28 tend to resist rearward movement of the plungers 36, 38, such that the pawl 50 swings in clockwise direction viewing FIGS. 1 and 2 against the pressure of the spring 52, and enables the chisel-shaped lower front edge to ride over the top of the teeth 40 as the arm 32 moves rearwardly.

A rear, upper end of the pawl 50 extends through a hole in the body 28. When it is desired to move the plungers 36, 38 in a rearwardly direction, such as in instances where the cartridge 24 has been emptied, the user may depress the rear end of the pawl 50 to swing the front edge of the pawl 50 upwardly and disengage the teeth 40. While the pawl 50 is depressed in this manner, the user can grasp block 42 to pull the plungers 36, 38 in a rearwardly direction away from the cartridge 24.

Turning now to the cartridge 24, the cartridge 24 includes a first or upper cylindrical container 56 and a second or lower cylindrical container 58. Both of the containers 56, 58 have an elongated, cylindrical inner chamber 60 with a rear circular opening 62 (FIG. 6). The containers 56, 58 (including the longitudinal axes of the chambers 60) lie in parallel, side-by-side relation to each other. Both chambers 60 also have a "D" shaped front opening separated from each other by an inner wall and surrounded by a protruding cylindrical neck 64.

The cartridge 24 also includes a rear, generally rectangular flange 66 that is illustrated in more detail in FIGS. 5 and 6. The flange 66 surrounds the rear opening 62 of the containers 56, 58, and optionally is of double-walled construction reinforced by integral webs. The flange 66 includes an elongated recess 68 that extends between the rear opening 62 of the containers 56, 58 from one side of the flange 66 to the other, and has a generally U-shaped configuration in transverse view. The recess 68 extends in a direction that is perpendicular relative to a reference line extending between centers of the rear openings 62 of the containers 56, 58.

The flange 66 is received in a complementally-shaped receptacle 70 (FIG. 5) of the applicator body 28. The receptacle 70 includes an elongated, raised tab 72 that matingly fits in the recess 68 as the flange 66 is inserted in the receptacle 70.

The recess 68 and tab 72 are useful in instances where it is desired that only cartridges 24 containing certain components of material are used with the applicator 22. As such, a cartridge having a rear flange of similar thickness but lacking the recess such as recess 68 would not fit in the receptacle 70 due to tab 72.

Other alternative key-like constructions are possible to insure that the applicator 22 is used only with certain cartridges such as cartridge 24. An example of an alternative construction is illustrated in FIG. 7, wherein flange 66a of cartridge 24a has two recesses 67a on each side and mate with two corresponding pin-like tabs located adjacent the receptacle in the applicator. Two pairs of recesses 67a are provided, so that the flange 66a can be inserted in the receptacle of the applicator in either of two direction.

The receptacle 70 that is depicted in FIGS. 1–2 and 5 is constructed to enable the cartridge 24 to be coupled to the applicator 22 while approaching the applicator 22 from its side (i.e., in a direction perpendicular and toward the plane of the drawing shown in FIGS. 1, 2 and 5). Other constructions are also possible. For example, the receptacle may open upwardly and the tab and recess may be oriented in a similar, upwardly direction, so that the flange is inserted into the receptacle as the cartridge is moved in a downwardly direction.

The front end of the cartridge 24 includes two "L" shaped ears 74 that are adapted to releasably engage a plate 76 of the static mixing assembly 26 and form a bayonet-style coupling. Before the static mixing assembly 26 is coupled to the cartridge 24, the ears 74 may be used to releasably engage a shipping cap. A suitable cap and an optional induction seal for covering the front openings of the containers 56, 58 are described in U.S. Pat. No. 5,236,108 that is assigned to the assignee of the present invention and that is expressly incorporated by reference herein. A suitable cap useful for shipping as well as for covering the front openings between uses is described in pending U.S. patent application Ser. No. 08/547,595 entitled "Dispensing Container and Sliding Cap Assembly", [attorney docket no. 51949USA3A] filed on even date herewith, the contents of which are expressly incorporated by reference herein.

The cartridge 24 is preferably integrally molded of an amorphous polyolefin such as is sold under the trade name "ZEONEX" grade 480 (from Nippon Zeon Co., Ltd., Tokyo, Japan). Alternatively, the cartridge can be made of a polyethylene such as is sold under the trade name "ALATHON H5618" (from Occidental Chemical Corporation, Dallas, Tex.), or a polypropylene resin such as is sold under the trade name "FINA 3467" (from Fina Oil and Chemical Company, Deer Park, Tex.). Further information regarding the cartridge material can be obtained in pending U.S. patent application Ser. No. 08/202,390 entitled "DELIVERY SYSTEM FOR WATER-CONTAINING DENTAL MATERIALS" [attorney's docket number 50605USA2A] filed on Feb. 28, 1994, the disclosure of which is expressly incorporated by reference herein.

The static mixing assembly 26 is illustrated in FIGS. 1 and 2, and the front end of the assembly 26 is also shown in the enlarged illustration of FIG. 3. The static mixing assembly includes an exit conduit 78 that is integrally connected to the plate 76. The exit conduit 78 includes a rear cylindrical chamber that fits over the neck 64 when the plate 76 is coupled to the ears 74. The exit conduit 78 also includes a second, somewhat smaller cylindrical chamber in front of the chamber surrounding the neck 64, and an internal cylindrical cavity 80 that extends forwardly from the second inner chamber of the exit conduit 78 toward a front opening 82.

The exit conduit 78 includes four spaced-apart, longitudinally extending strengthening ribs 84 that integrally interconnect the plate 76 and a middle portion of the exit conduit 78. The plate 76 has a somewhat oval-shaped configuration, and the thickness of the portion of the plate 76 that fits behind the ears 74 varies, so as the plate 76 is placed over the neck 64 and turned about the longitudinal axis of the exit conduit 78, the plate 76 releasably locks into tight engagement with the front end of the cartridge 24.

The plate 76 and the ears 74 together comprise a coupling that is shiftable between a locked orientation wherein the static mixing assembly 26 is non-releasably connected to the cartridge 24 and an unlocked orientation wherein the static mixing assembly may be released from the cartridge. Other couplings are also possible and will be apparent to those knowledgeable in the art. For example, the coupling may comprise a threaded, flared fitting with a nut, or a fitting with a sliding, lockable collar.

A static mixing element 86 is received in the cavity 80 of the exit conduit 78. The static mixing element 86 includes an integrally joined series of helical, auger-like or "bow-tie" mixing segments that successively subdivide, rotate and recombine the incoming component streams. The static mixing element 86 is held in place in the cavity 80 by frictional engagement with inner walls of the cavity 80. A suitable material for the exit conduit 78 is an acetal resin such as is sold under the trade name "DELRIN" (E. I. dupont de Nemours & Co.) while the static mixing element 86 may be made of polypropylene.

An elongated, metal cannula 88 extends outwardly from the front opening 82. As shown in FIG. 3, the cannula 88 has an outwardly flared rear section 90 that is located in the cavity 80 adjacent and rearwardly of the front opening 82. The flared rear section 90 engages an inner, conical wall section of the cavity 80 in front of the static mixing element 86, where the exit conduit 78 is necked down in tapered fashion.

The cannula 88 is elongated and curved in a direction along its longitudinal axis as illustrated in the drawings. Other configurations are also possible, including straight or angled configurations. Preferably, the cannula 88 is bendable as needed by finger pressure. The cannula 88 is swivelable about its longitudinal axis relative to the exit conduit 78.

The flared rear section 90 of the cannula 88 substantially precludes the cannula 88 from detaching from the exit conduit 78 by movement in a forwardly direction. The flared rear section 90 also enables the cannula 88 to swivel about its longitudinal axis relative to the exit conduit 78. The static mixing element 86, located behind the flared rear section 90, substantially prevents the cannula 88 from moving in a rearward direction to an orientation wholly within the cavity 80, as might occur, for example, when the cannula 88 is unintentionally pressed against another object. Such construction provides for easy assembly during manufacture, and eliminates the need for other parts to retain the cannula 88 in place.

An alternate embodiment of the invention is illustrated in FIG. 4, wherein static mixing assembly 26b includes an exit conduit 78b that is curved in directions along its length. The exit conduit 78b contains a static mixing element 86b that, when in place in the exit conduit 78b, is also curved along its length. The static mixing element 86b may be injection molded in the curved configuration as illustrated in FIG. 4. Alternatively, the static mixing element 86b may be injection molded in a straight configuration as is illustrated in FIG. 3, and then bent to the curved configuration illustrated in FIG. 4 as it is inserted within the exit conduit 78b.

Other aspects of the static mixing assembly 26b are substantially the same as the static mixing assembly 26 described above. The static mixing assembly 26b is particularly advantageous in instances where its curved configuration facilitates access to certain regions of the oral cavity.

In use of the system 20, the handle 30 is gripped by the fingers of the user while the arm 32 contacts rear portions of the user's palm and an adjacent, opposing section of the user's thumb. As the arm 32 is moved toward the handle 30, the plungers 36, 38 advance and cause the heads 46 to push pistons 92 (FIG. 2) in the chambers 60 in a forwardly direction toward the neck 64. As the pistons 92 advance, components of a dental material that are located in the chambers 60 are expelled from the cartridge 24 and directed through the exit conduit 78, wherein the static mixing element 86 combines the two components to form the uniformly mixed, homogeneous dental material that is then expelled from a front discharge opening of the cannula.

Figure 8:
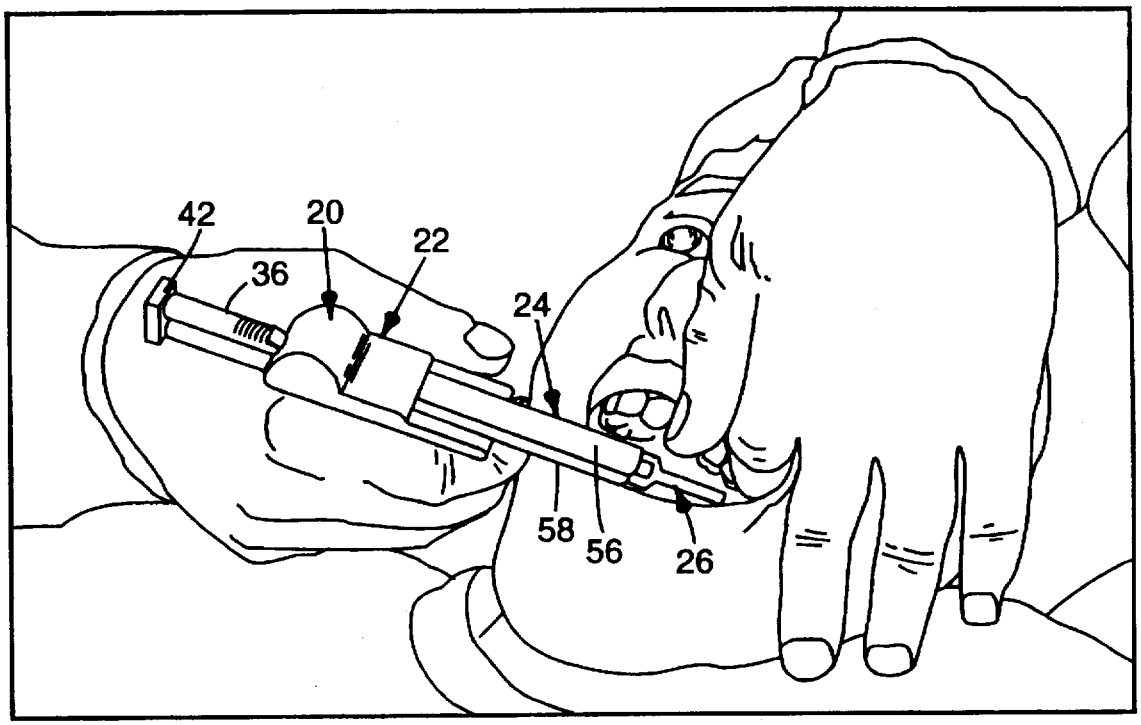
FIG. 8 is a reduced perspective view illustrating one example of a use of the present invention with a dental patient.

FIG. 8 illustrates one example of the use of the dispensing system 20. As shown, the over-under orientation of the containers 56, 58 enables the longitudinal axes of the chambers 60 to be oriented in a side-by-side, mesial and distal relationship to each other relative to mesial and distal directions in the patient's oral cavity. In some instances, the containers 56, 58 will be oriented substantially parallel to the patient's occlusal plane. Simultaneously, and while dispensing the dental material into the patient's oral cavity, the user holds the applicator 22 in an orientation wherein the handle 30 is generally parallel to the patient's occlusal plane.

The over-under configuration of the dispensing system 20 as illustrated in FIG. 8 is particularly advantageous in many instances in the dental operatory, such as when the patient is reclining in a chair and the dentist or dental assistant is approaching the patient from the rear (i.e., is standing behind the patient's head). In such circumstances, alignment of the containers 56, 58 in a side-by-side mesial and distal orientation enables the front end of the cartridge 24 to easily reach inside the patient's oral cavity without the necessity of the patient opening his or her jaws to a relatively wide extent.

Figure 9:
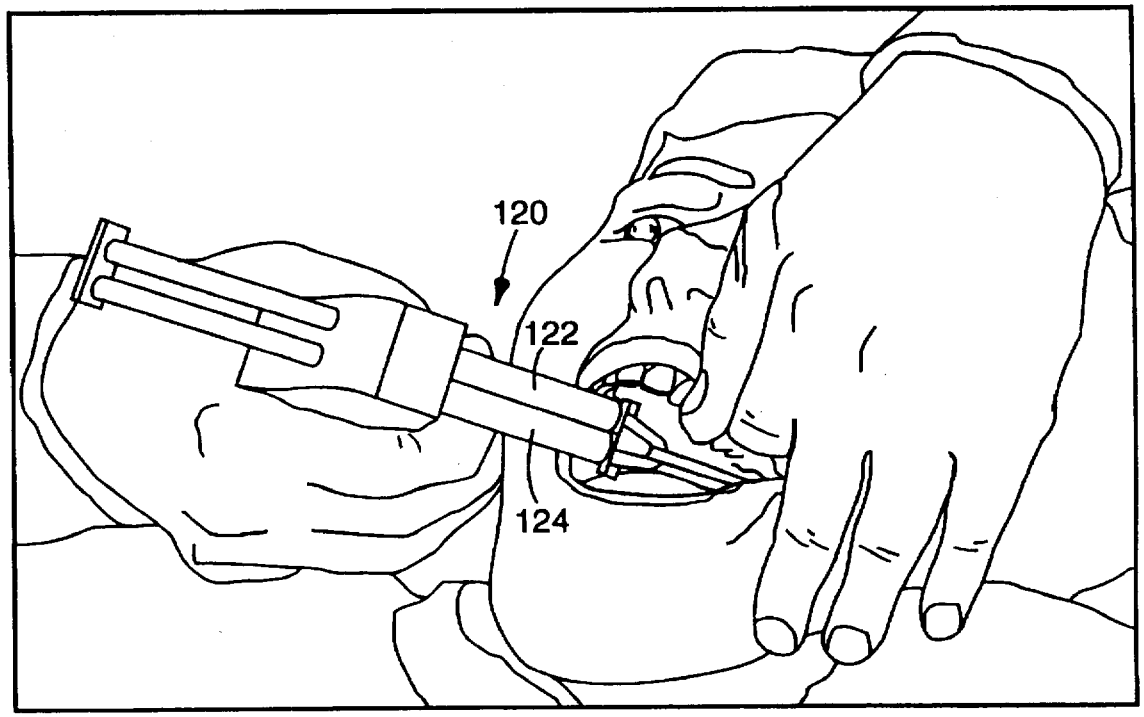
FIG. 9 is a reduced perspective view illustrating, for comparative purposes, the use of a dental dispensing system having two containers oriented in accordance with the teachings of prior art.

FIG. 9 depicts for comparative purposes a dispensing system 120, wherein containers 122, 124 of a dispensing cartridge are oriented similar to conventional double barrel dental dispensing systems typically used for impression material. In system 120, the longitudinal axes of the containers 122, 124 lie in a plane that is substantially perpendicular to the direction of extension of the dispensing system's handles. As such, when the user approaches the patient from the rear in the manner shown in FIG. 9, the containers 122, 124 are oriented in an occlusal-gingival relationship to each other relative to occlusal and gingival directions in the patient's oral cavity, with the result that the patient must open his or her jaws to a far greater extent than the extent afforded by use of dispensing system 20.

Inasmuch as some patients experience difficulty in opening their jaws as widely as is shown in FIG. 9, or are unable to hold their jaws in such an orientation for an extended period of time, use of the over-under configuration illustrated in FIG. 8 provides a significant advantage both to the practitioner as well as to the patient. Alignment of the longitudinal axes of the containers 56, 58 in a common plane that is parallel to the direction of extension of the handle 30 and the arm 32 enables the system 20 to be particularly satisfactory in instances where dental material is dispensed directly into the oral cavity. Also, the present invention often affords better visibility while working in the posterior section of the mouth.

Location of the pivot 34 above the plungers 36, 38 enables the user's hand to grasp the applicator 22 in close proximity to the cartridge 24 to facilitate maneuvering the cannula 88 and enhance control over the placement of the dispensed material. In addition, location of the pivot 34 above the plungers 36, 38 enhances the user's leverage when squeezing the arm 32 toward the handle 30. Provision of the forward stationary handle 30 and recessing the flange 66 behind the handle 30 enable the user to optionally rest his or her fingers against the patient's cheeks as shown in FIG. 8 to help steady the system 20 during a dispensing operation.

The invention is useful for two part dental paste and/or liquid systems. It is especially useful for two part glass ionomer pastes that have general applicability as restoratives, liners, bases, cements, sealants, core build-up materials and dental or orthodontic adhesives.

An applicator for dispensing material from a cartridge according to another embodiment of the invention is broadly designated by the numeral 210 in FIGS. 10-14. The applicator 210 includes a housing or body 212 that has a hollow upper portion and a depending handle 214 that is fixed to the upper portion. The body 212 is constructed of two joined-together sections that are integrally molded of a synthetic resinous material (such as "RADEL" brand polyphenylsulfone, no. R5100; from Amoco).

Figure 12:
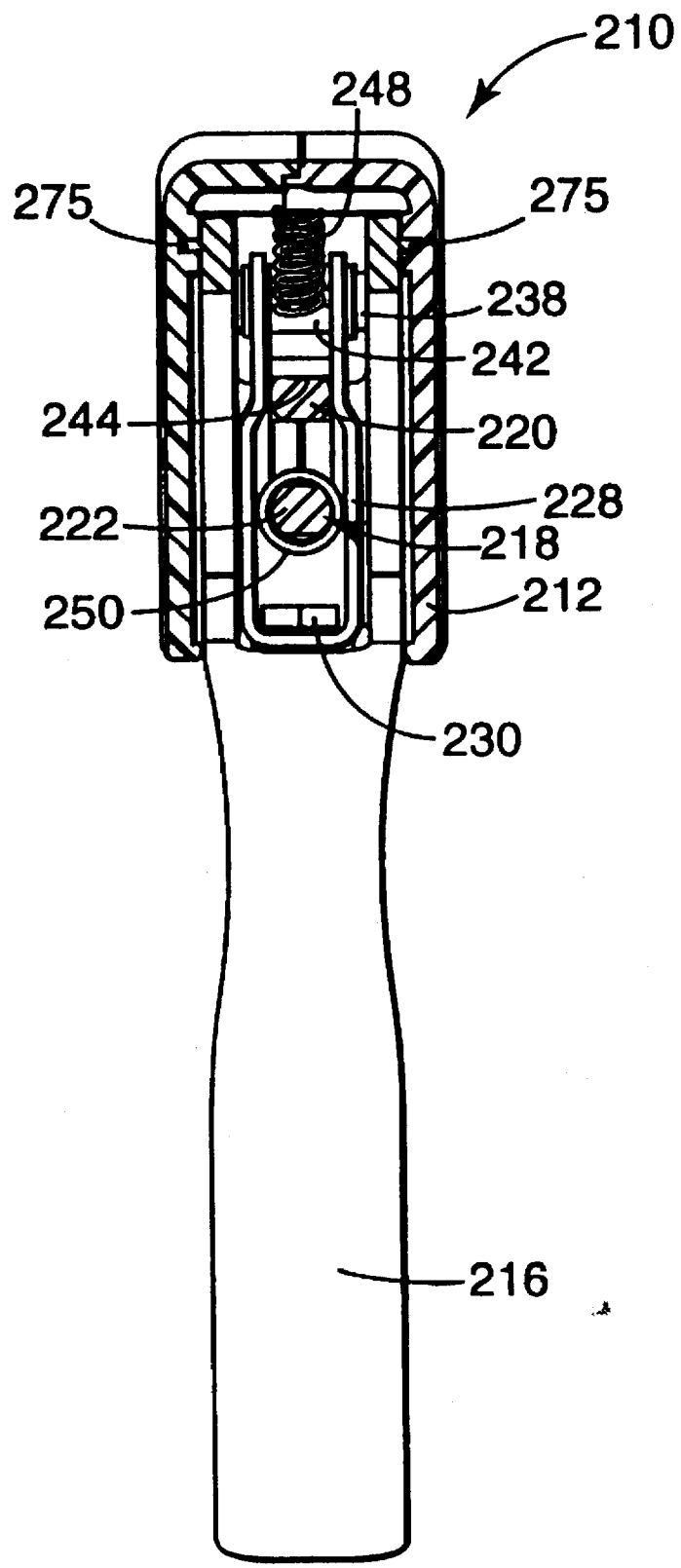
FIG. 12 is an elevational view in partial section of the applicator shown in FIG. 11, taken along lines 12—12 of FIG. 11.

The applicator 210 also includes an arm 216 that depends from the upper portion of the body 212 and is located next to the handle 214. An upper portion of the arm 216 is bifurcated and straddles opposite sides of a plunger device 218. A lower portion of the arm 216 is hollow and presents a recess. As shown in FIG. 12, each side of the upper, bifurcated portion of the arm 216 has an outwardly extending cylindrical boss 275 that is received in a socket of the body 212 for pivotally coupling the arm 216 to the body 212.

The plunger device 218 includes an upper and lower plungers 220, 222 respectively that are integrally connected together by a handle or ring 224. Both of the plungers 220, 222 pass through respective pairs of aligned holes formed in the upper portion of the body 212. Each plunger 220, 222 includes an enlarged, forward head for engaging pistons in the container. Each head is larger than the holes in the body 212 so that the plungers 220, 222 cannot be inadvertently detached from the body 212. The top of the upper plunger 220 also has a row of flat teeth 226.

Figure 11:
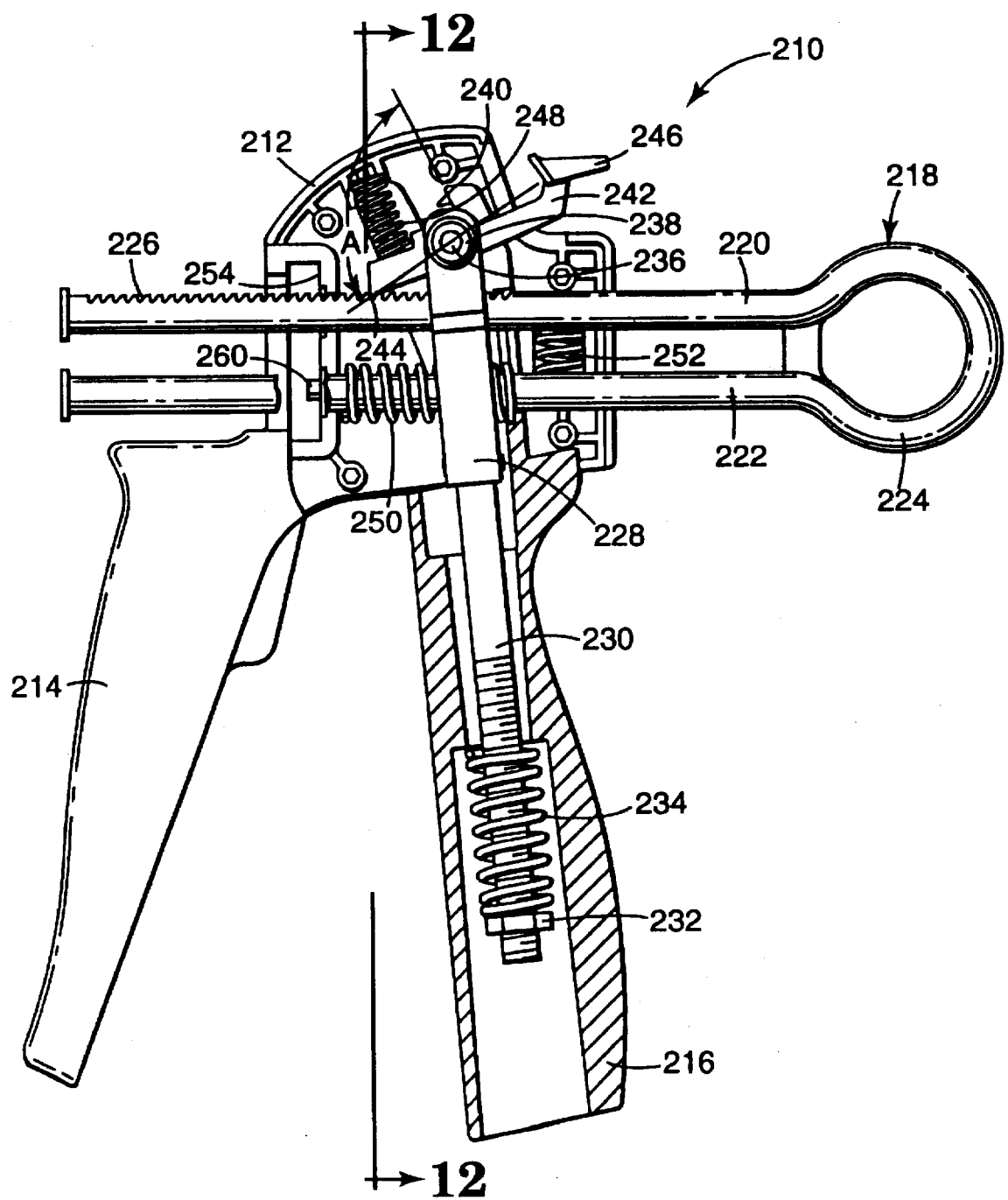
FIG. 11 is a side elevational view in partial section of the applicator shown in FIG. 10, wherein the cartridge and static mixing assembly have been removed.

A yoke 228 of a clutch of the applicator 210 extends along both sides of the plungers 220, 222 within the hollow portion of the body 212 and within the upper bifurcated portion of the arm 216. A lower crossbar of the yoke 228 has a hole that receives a shaft of a bolt 230. As illustrated in FIG. 11, the bolt 230 includes a head that rests against the crossbar of the yoke 228, and the lower threaded portion of the bolt 230 receives a nut 232. A coiled compression clutch spring 234 surrounds the bolt 230 and bears against the nut 232 as well as a shoulder formed in the hollow recess of the arm 216.

A pivot pin 236 extends through aligned holes of the upper, spaced apart ends of the yoke 228, and each end of the pivot pin 236 extends through a bushing 238. Each of the two bushings 238 is received in a slot 240 of a respective one of the upper bifurcated end portions of the arm 216.

A ratchet mechanism of the applicator 210 includes a follower or pawl 242. A central portion of the pin 236 extends through a hole of the pawl 242. The pawl 242 includes a chisel-shaped lower front edge 244 for engagement with the upper plunger 220 in the spaces between adjacent teeth 226. A rear, upper portion of the pawl 242 extends through an opening in the body 212 and terminates as a tab 246.

A coiled compression ratchet spring 248 urges the front edge 244 of the pawl 242 into releasable engagement with the teeth 226. The ratchet spring 248 extends between an upstanding boss that is located on a top surface of a front portion of the pawl 242 and a depending socket that is molded on the upper inside wall of the body 212, both of which serve to retain the ratchet spring 248 in place. The ratchet spring 248 urges the pawl 242 in a counter-clockwise direction (viewing, for example, FIG. 11) in an arc about the pivot pin 236. As an alternative, the spring 248 could be replaced by a coil spring similar in shape and placement to the spring 52 shown in FIG. 2 (so long as a pivot pin or other supporting structure for the coil spring is also provided).

A coiled compression return spring 250 is located in the hollow portion of the body 212 and is received around a portion of the lower plunger 222. A front end of the return spring 250 bears against the inner wall of the body 212, while a rear end of the return spring 250 bears against an upper, rear portion of the arm 216. The return spring 250 urges the arm 216 in a counter-clockwise direction (viewing, for example, FIGS. 10-11) in a rearwardly direction away from the handle 214 and in an arc about the pivot bosses 275.

A coiled compression drag spring 252 is also located within the hollow upper portion of the body 212 and bears against adjacent sides of the plungers 220, 222. The drag spring 252 is retained in place by inner projections formed in the body 212. The drag spring 252 functions to hinder rearward movement of the plungers 220, 222 when the arm 216 is released for movement of the front edge 244 in a rearward direction along the row of teeth 226, as may occur when it is desired to advance the ratchet mechanism for subsequent additional forward movement of the plungers 220, 222. Preferably, the springs 234, 248, 250, 252, the pawl 244, the arm 216, the plunger device 218 and other components of the applicator 210 other than the body 212 are made of a metallic material (such as stainless steel) that is suitable for repeated autoclaving or chemical sterilization.

Figure 10:
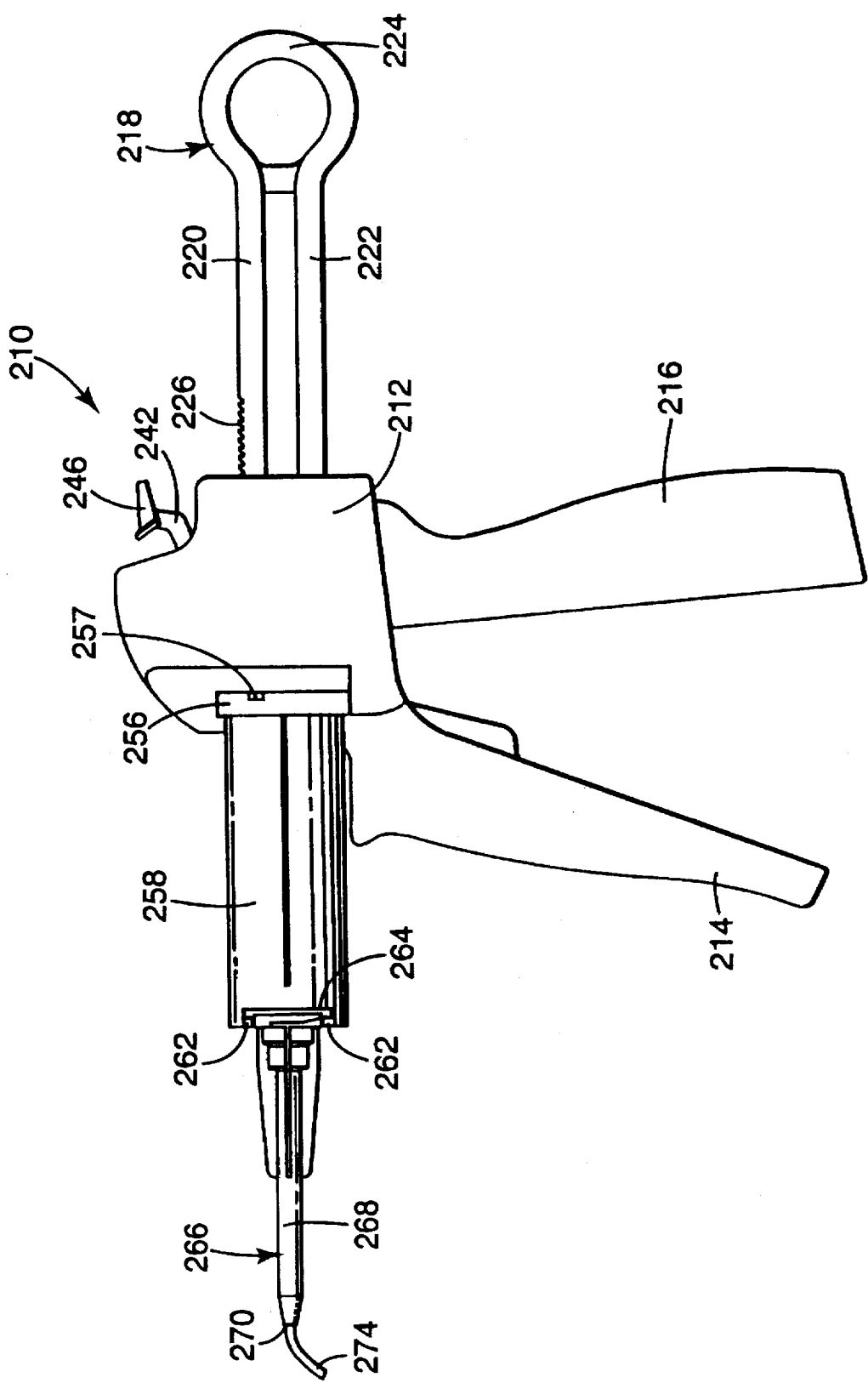
FIG. 10 is a side elevational view of an applicator having a clutch constructed in accordance with another embodiment of the present invention, and also showing a dispensing cartridge and static mixing assembly coupled to the applicator.
Figure 15:
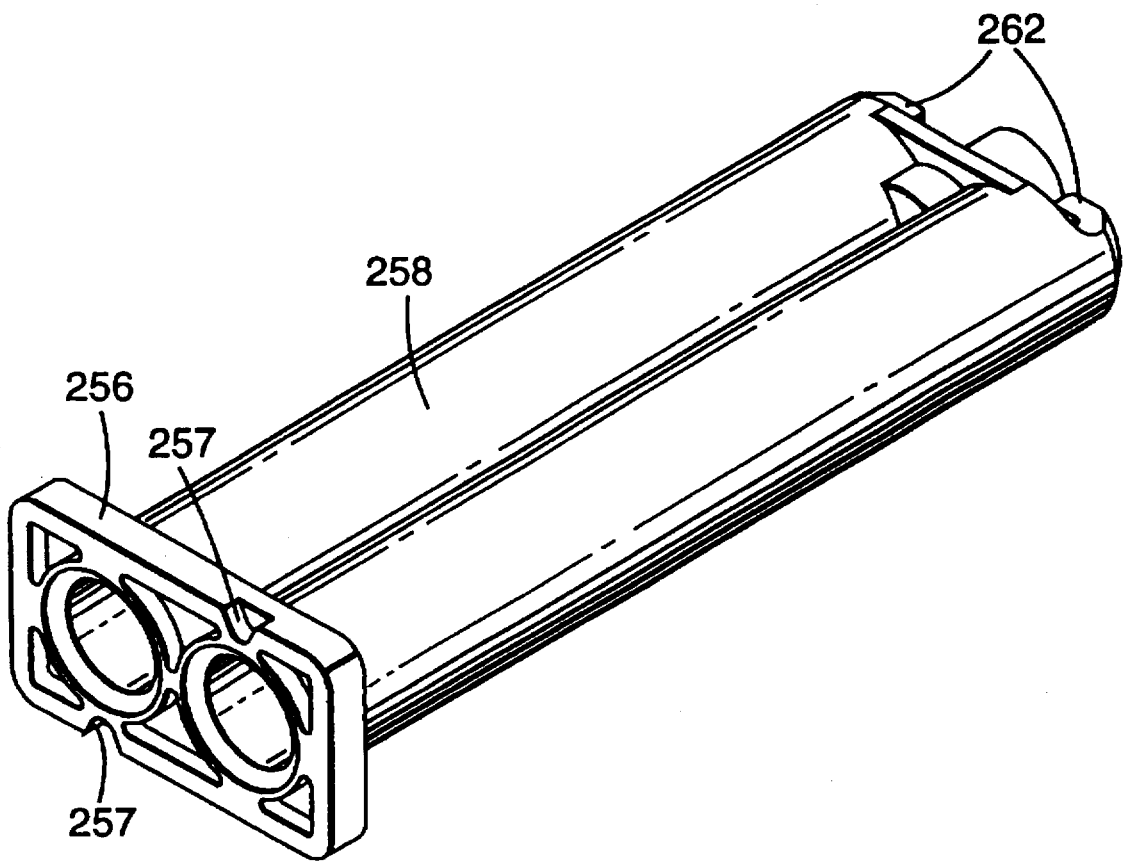
FIG. 15 is an enlarged perspective view of the dispensing cartridge alone that is depicted in FIG. 10.
Figure 16:
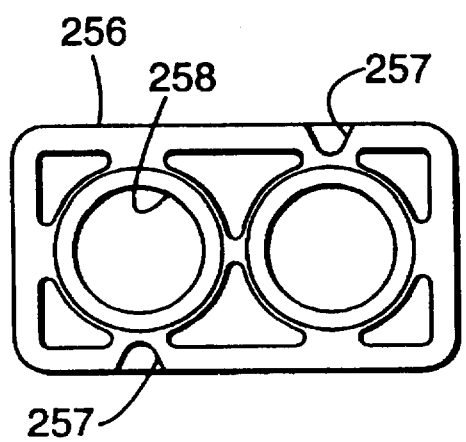
FIG. 16 is a rear view of the cartridge illustrated in FIG. 15.

The applicator body 212 includes a generally C-shaped receptacle 254 that complementally receives a flange 256 of a double-barrel cartridge 258 which is shown in FIGS. 10 and 15-16. The flange 256 includes two recesses 257 located on opposite sides of the flange 256. The cartridge 258 includes an upper container having a cylindrical chamber and a lower container having cylindrical chamber that lie in parallel, side-by-side relation to each other, and a piston (not shown) is received in each chamber. Each chamber contains a different component of the material to be mixed and dispensed.

Each recess 257 extends inwardly from the rear end of the flange 256 as well as from a respective side of the flange 256. The flange 256 has a webbed construction that comprises a front plate surrounding a rear end portion of the containers, a generally rectangular structure extending about the periphery of the flange 256 and two circular structures that are integrally joined to (and form part of) the end portions of the containers as well as to adjacent portions of the generally rectangular structure and the front plate. Each recess 257 extends into the generally rectangular structure on a long side of the flange 256 in a location directly adjacent one of the two circular structures. Each recess 257 extends inwardly toward the central longitudinal axis of the adjacent chamber, and has a generally U-shaped configuration in a reference plane perpendicular to the longitudinal axes. The cartridge 258 including the flange 256 is preferably integrally molded of a material such as described above in connection with the cartridge 24.

The body 212 includes a tab 260 that is shown in FIG. 11. The tab 260 is located in the receptacle 254 and is behind the lower plunger 222 in FIGS. 13 and 14. The tab 260 is matingly received in one of the two recesses 257 of the flange 256 as the flange 256 is received in the receptacle 254.

The front end of the container 258 includes two "L" shaped ears 262 that are adapted to releasably engage a plate 264 of a static mixing assembly 266. The plate 264 and the ears 262 together form a bayonet-style, lockable coupling shiftable between a locked orientation and an unlocked orientation. The ears 262 are similar to the ears 74 described above.

The static mixing assembly 266 includes an exit conduit 268 that is integrally connected to the plate 264. The exit conduit 268 includes a rear cylindrical chamber that fits over a neck of the cartridge 258 when the plate 264 is connected to the ears 262. The exit conduit 268 also includes a second, somewhat smaller cylindrical chamber in front of the chamber surrounding the neck, and an internal cylindrical cavity of the exit conduit 268 extends forwardly from the second inner chamber toward a front opening 270.

The plate 264 has a somewhat oval-shaped configuration, and the thickness of the portion of the plate 264 that fits behind the ears 262 varies. As the plate 264 is placed over the neck of the cartridge 258 and as the exit conduit 268 is turned about its longitudinal axis, the plate 264 releasably locks into tight engagement with the cartridge 258 between the ears 262 and a front end of the cartridge 258. The exit conduit 268 also includes four spaced-apart, longitudinally extending strengthening ribs that integrally connect the plate 264 and a middle portion of the exit conduit 268.

A static mixing element (not shown) is received in a cavity of the exit conduit 268 and is similar to the static mixing element 86 described above. The static mixing element may be made of polypropylene (such as "PROFAX" brand, no. 6331NW; from Himont USA, Wilmington, Del.) and have an appearance similar to that shown in U.S. Pat. No. 4,538,920. A suitable material for the exit conduit 268 is nylon (such as "ZYTEL" brand, no. 101L; from DuPont) that is tinted to an orange color to block passage of actinic radiation.

An elongated, metal cannula 274 extends through and outwardly away from the front opening 270. The cannula 274 is similar to the cannula 88 mentioned above and has an outwardly flared rear section that is located in the cavity of the exit conduit 268 between the front of the static mixing element and the opening 270. The flared rear section of the cannula 274 engages an inner, conical wall section of the cavity of the exit conduit 268, where the exit conduit 268 is necked down in tapered fashion.

Figure 13:
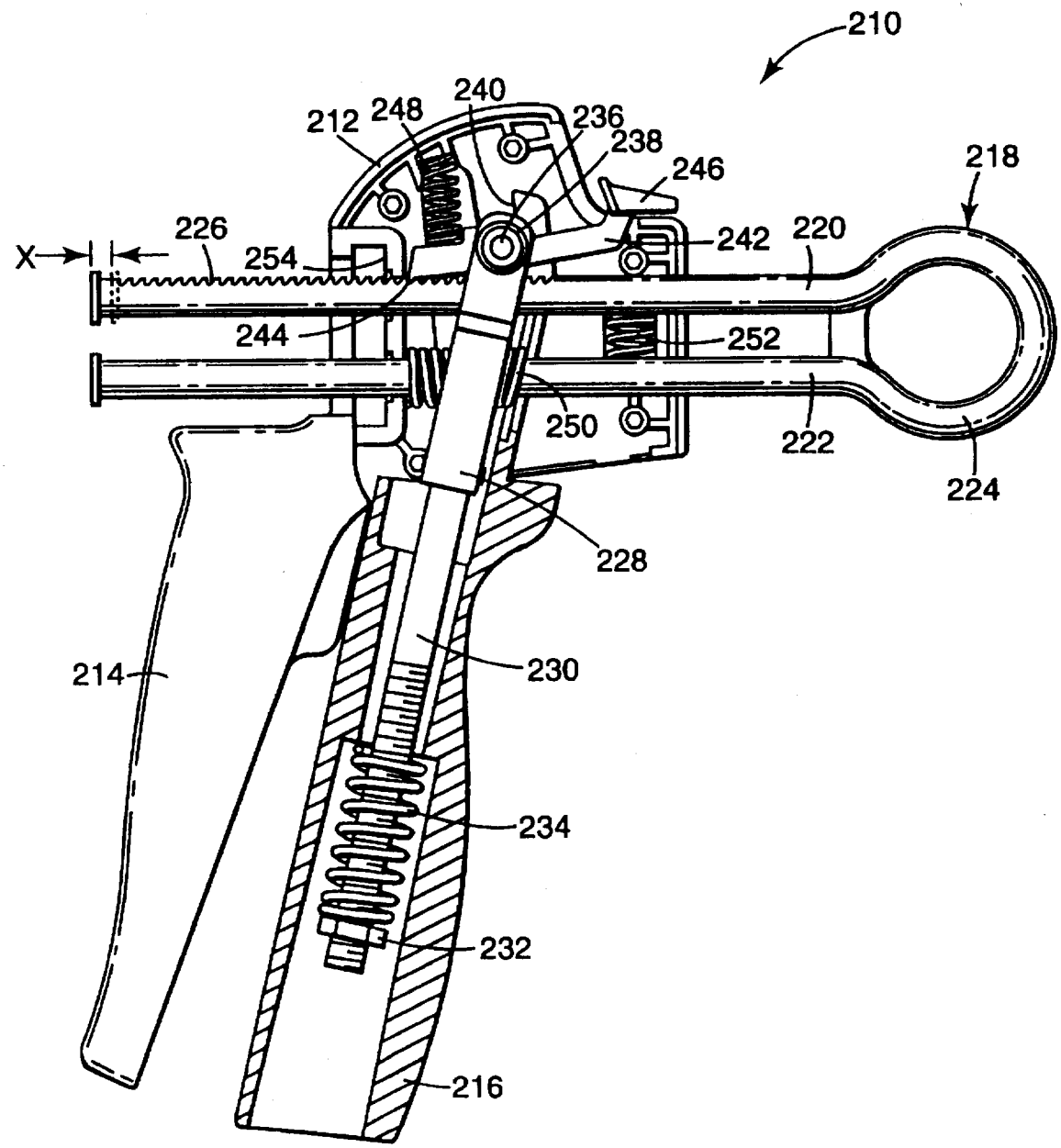
FIG. 13 is a view somewhat similar to FIG. 11 except that a handle of the applicator has been moved about a pair of pivot bosses, causing a pawl to advance a pair of plungers of the applicator.

In use, the applicator 210 is grasped by the handle 214, and the arm 216 is pivoted approximately 20° in an arc about the bosses 275 from the initial, rest orientation as is illustrated in FIG. 11 and to a forward orientation as is shown in FIG. 13. The front edge 244 of the pawl 242 drivingly engages the teeth 226 during movement of the arm 216 toward the handle 214 in order to advance the plungers 220, 222. The angle designated "A" in FIG. 11 represents the angle between a first reference plane extending between the pivot pin 236 and the front pawl edge 244 and a second reference plane parallel with edges of the arm 216 that define the slot 240. The angle A is greater than 90°.

As the arm 216 is moved to its forward orientation as depicted in FIG. 13, the pawl 242 moves the plungers 220, 222 forward a distance designated "X". The moving plungers 220, 222 advance the pistons in the cartridge 258, such that material in each chamber of the cartridge 258 is directed to the static mixing assembly 266 and ultimately through the cannula 274 in order to dispense the material.

Upon release of the arm 216, the return spring 250 urges the arm 216 in a rearward direction away from the handle 214 and back to its initial rest orientation as shown in FIG. 11. Frictional engagement of the drag spring 252 with the plungers 220, 222 tends to restrict rearward movement of the plungers 220, 222 to a degree sufficient to enable the front edge 244 of the pawl 242 to slightly swing in a clockwise direction viewing FIGS. 11 and 13–14, so that the front edge 244 rides over the top of the teeth 226 as the arm 216 moves rearwardly.

When it is desired to move the plungers 220, 222 in a rearwardly direction, the user may depress the tab 246 in order to pivot the pawl 242 in a clockwise direction and disengage the front edge 244 from the teeth 226. When the tab 246 is depressed in this manner, the user can grasp the ring 224 to pull the plungers 220, 222 in a rearwardly direction.

Figure 14:
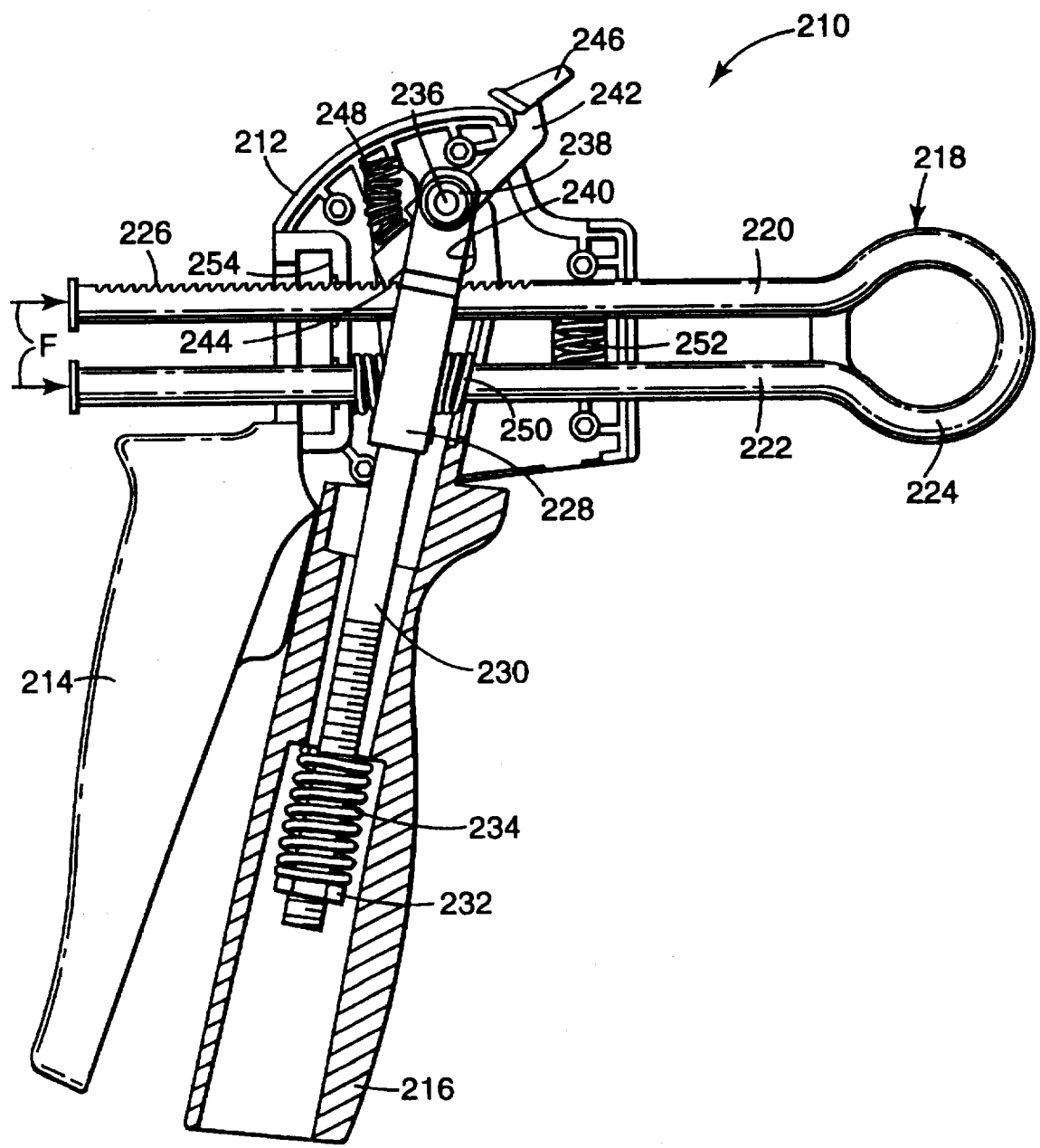
FIG. 14 is a view somewhat similar to FIG. 13 except that the clutch is shown as activated in order to preclude further advancement of the plungers, as may occur whenever movement of the plungers is hindered by resistance that is greater than a certain value.

FIG. 14 shows an illustration for exemplary purposes of the clutch of the applicator 210 in its fully activated position when the arm 216 is pivoted in an arc approximately 20° about the bosses 275. The force designated "F" in FIG. 14 represents a resistive force that is preferably less than a force that would burst the cartridge 258 or break, strain or otherwise damage components of the applicator 210. Preferably, the sum of the forces "F" sufficient to activate the clutch is any force that is in the range of 45–60 kg.

When the plungers 220, 222 encounters the forces "F", the pawl 242 pivots in a counter-clockwise direction (when viewing FIG. 14) about the front edge 244 of the pawl 242. The sum of the forces "F" is sufficient to overcome the friction between the bushings 38 and the slots 40 and the bias presented by the clutch spring 234 and enable the pivot pin 236 (along with the yoke 228) to rise in the slot 240 as the arm 216 continues to pivot toward its forward orientation. The sum of the forces "F" is also sufficient to overcome the relatively small bias presented by the pawl spring 248. As the yoke 228 rises within the hollow portion of the housing 212, the bolt 230 moves upwardly within the hollow recess of the arm 216 and compresses the clutch spring 234 as shown in FIG. 14.

Consequently, the clutch of the applicator 210 enables energy as provided by the user to move the arm 216 to be transferred to the pivotal motion of the pawl 242 about the front edge 244, as well as to the upward movement of the bolt 230 against the biasing force of the clutch spring 234 whenever the sum of the resistive forces "F" is greater than a certain value such as 45 kg. In such an instance, energy supplied by the arm 216 is no longer used to advance the plungers 220, 222. Advantageously, the clutch operates in a smooth manner during activation, without a snap or toggle feeling as may be imparted by other clutch constructions.

The upward movement of the pawl 242 during activation of the clutch enables the tab 246 to rise and thereby provide a visual indication to the user that the force supplied to the arm 216 is excessive and greater than a certain design value. Optionally, an upstanding projection can be connected to the pawl 242 in a location between the tab 246 and the pivot pin 236, and the projection could pass through a hole in the top of the body 212 and be painted with a red color or provided with other identifying means to provide a greater visual indication that the clutch has been activated. Upon release of the arm 216, the clutch spring 234, the return spring 250 and the pawl spring 248 enable the handle 214 and the pawl 242 to return to their initial, rest positions as illustrated in FIG. 11.

As an alternative, the pawl spring 248 and the clutch spring 234 may be replaced by a single spring that is located in the area where the pawl spring 248 is shown in the drawings. Such construction would also enable the bolt 230 and the yoke 228 to be eliminated. However, such a combination pawl and clutch spring may need to be significantly larger in many instances than the pawl spring 248 shown in the drawings such that the top of the body 212 would need enlargement for accommodating the combination pawl and clutch spring. By contrast, the embodiment shown in the drawings is advantageous because the top portion of the body 212 is relatively small and does not unduly obstruct the view toward the site where the material is to be dispensed. The recess in the arm 216 has sufficient space to easily receive the clutch spring 234.

The tension on the clutch spring 234 may be adjusted by rotation of the nut 232. In this manner, the total amount of the resistive forces "F" needed to activate the clutch can be varied as needed. Preferably, the nut 232 is adjusted in the factory to a desired specification, and subsequently is either covered or provided with a non-standard outer configuration to discourage adjustment by a casual user.

Figure 17:
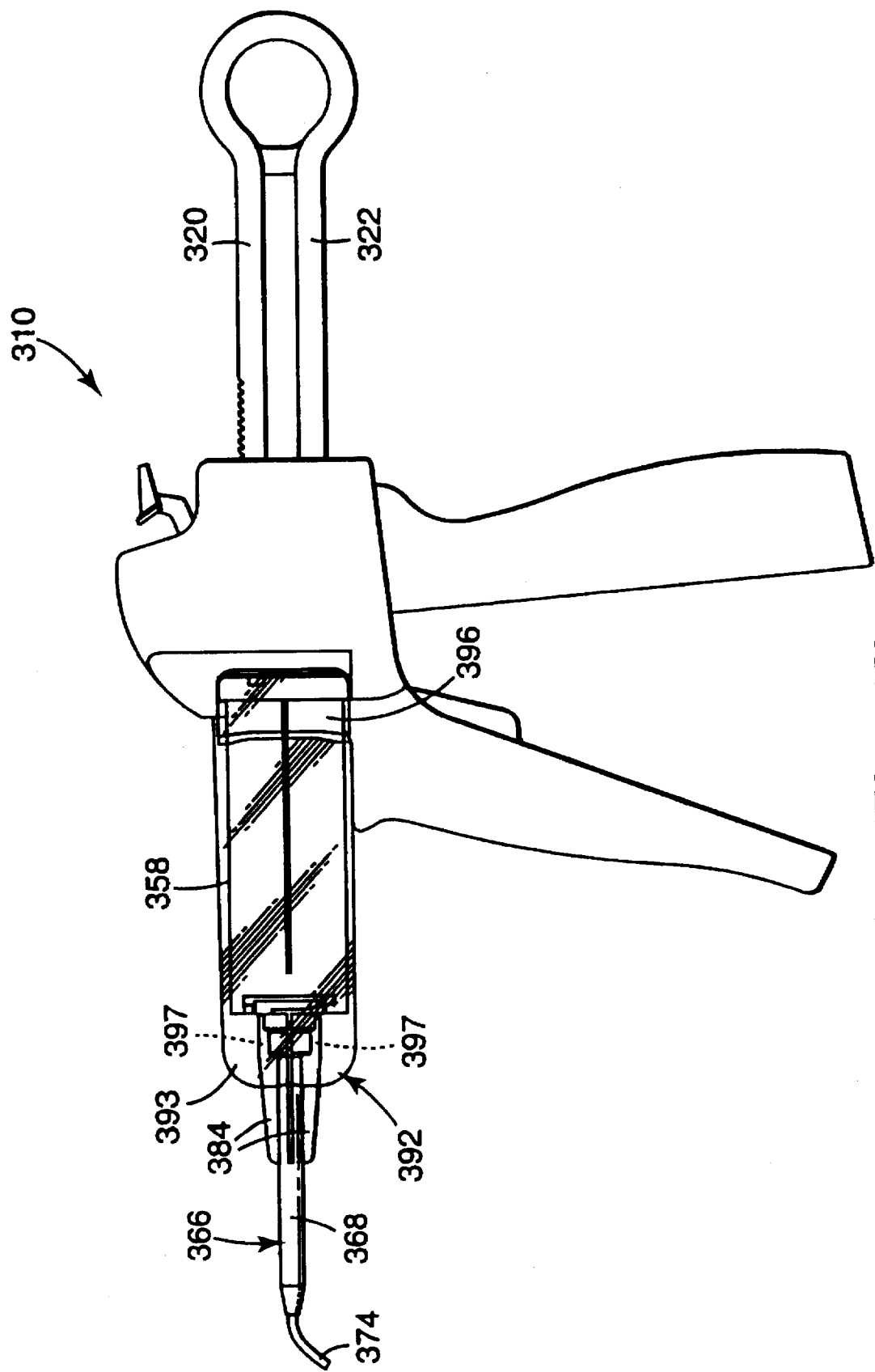
FIG. 17 is a side elevational view of a dispensing system according to another embodiment of the invention.

A dispensing system according to another embodiment of the invention includes an applicator 310 that is illustrated in FIG. 17. This dispensing system also includes a replaceable cartridge 358 that is removably received in a receptacle of the applicator 310, and a discharge tip that, in the embodiment shown, is a static mixing assembly 366. The cartridge 358 and the static mixing assembly 366 are identical to the cartridge 258 and the static mixing assembly 266 described in connection with the embodiment shown in FIGS. 10–16, and as such a detailed description of each need not be repeated. The applicator 310 is identical to either the applicator 210 or alternatively to the applicator 410 described below.

Figure 18:
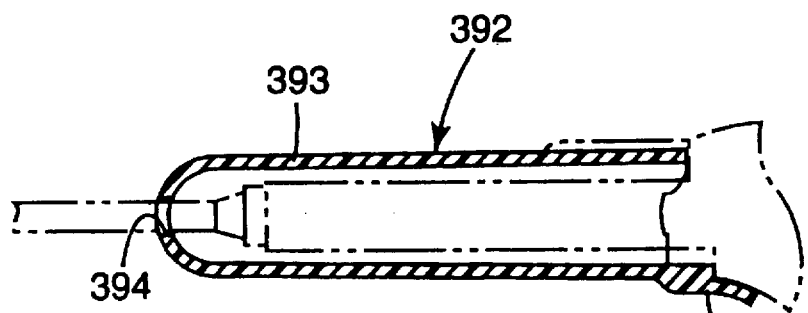
FIG. 18 is an enlarged cross-sectional view taken in the horizontal reference plane of a hygienic sheath of the system illustrated in FIG. 17, wherein an applicator, cartridge and discharge tip of the system are shown in phantom lines.
Figure 19:
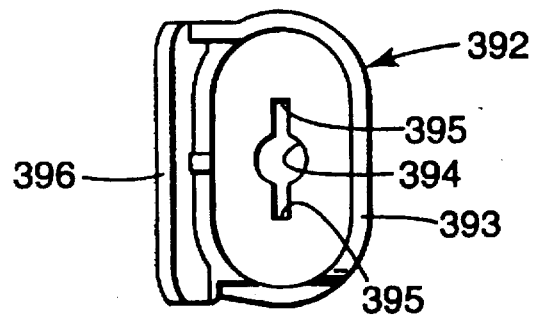
FIG. 19 is an end elevational view of the sheath depicted in FIG. 18.
Figure 20:
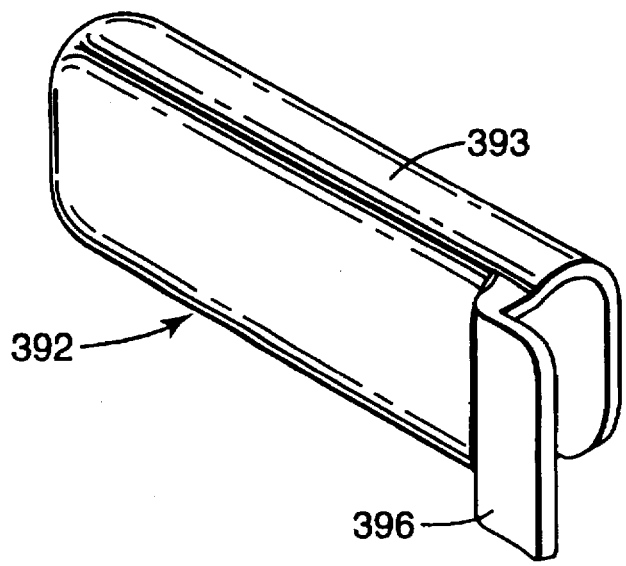
FIG. 20 is a top, left side and end perspective view of the sheath shown in FIGS. 18–19.

The dispensing system that is illustrated in FIG. 17 also includes a hygienic infection control sheath 392 that is also shown alone in FIGS. 18–20. The sheath 392 includes a hollow, tubular body 393 with a rearwardly extending shield portion 396. The front of the body 393 has an opening 394 (FIGS. 18–19) that includes a central circular aperture and two elongated slots extending vertically from opposite sides of the central aperture.

When the sheath 392 is in use as shown in FIG. 17, the sheath 392 extends over both barrels or containers of the cartridge 358 as well as a rear portion of the static mixing assembly 366. The body 393 has a configuration complemental to the outer shape of the cartridge 358. As shown in FIG. 17, the shield portion 396 extends over the rear flange of the cartridge 358 and preferably also covers a substantial majority of the side opening of the receptacle of the applicator 310.

The opening 394 of the sheath 392 includes two edge portions 395 that are best observed in FIG. 19. When the sheath 392 is placed over the cartridge 358 and the static mixing assembly 366, the edge portions 395 are in interference fit relation with respective upper and lower edge sections 397 of two strengthening ribs 384 that integrally interconnect a rear plate and a middle portion of an exit conduit 368 on opposite sides of the latter. Preferably, the material of the sheath 392 including the edge portions 395 has a higher Young's modulus than the Young's modulus of the material of the exit conduit 368 including the ribs 384.

The sheath 392 is preferably made of a rigid, autoclavable material that is transparent or translucent so that the practitioner can identify the shade of material in the cartridge. Suitable materials include "RADEL" brand polyphenylsulfone, No. R5000; from Amoco, which has a Young's modulus (or modulus of elasticity) of $3.4\times10^5$ psi. By comparison, the exit conduit 368 when integrally molded of the "DELRIN" brand acetal resin described earlier has a Young's modulus of $1.75\times10^5$ psi. A satisfactory interference fit relation can be established when, for example, the distance between the edge portions 395 of the body 393 is 0.433 inch (11.0 mm), while the distance between the edge sections 397 of the strengthening ribs 384 is 0.450 inch (11.4 mm).

The relatively higher Young's modulus of the edge portions 395 of the sheath opening 394, being greater than the Young's modulus of the strengthening ribs 384, is an advantage because any substantial wear or permanent deformation due to the aforementioned interference fit will occur on the edge sections 397 instead of the edge portions 395. As such, the opening 394 of the sheath 392 will retain its configuration over an extended period of time and after many uses in the dental arena. By contrast, the static mixing assembly 366 is typically disposed of after a single use, and as a result any wear or deformation on the strengthening ribs 384 of the static mixing assembly 366 is of no concern.

The shape of the opening 394 permits passage of the cannula 374 of the static mixing assembly 366 so long as the slots of the opening 394 are substantially aligned with a reference plane that contains the central, curved longitudinal axis of the cannula 374. However, once the sheath 392 is in place as depicted in FIG. 17, the shape of the opening 394 prevents rotative movement of the ribs 384 and hence the static mixing assembly 366 relative to the cartridge 358 in reference planes laterally of the direction of movement of the plungers 320, 322. Thus, the sheath 392 when placed as shown in FIG. 17 retains the bayonet-type coupling that connects the static mixing assembly 366 to the cartridge 358 in a locked orientation.

As a result, the shape of the sheath opening 394 substantially prevents misalignment and improper coupling of the sheath 392 to the static mixing assembly 366, and essentially insures that the flange of the static mixing assembly 366 is fully, tightly and properly engaged with the ears of the cartridge 358. Such construction provides assurance that the static mixing assembly 366 will remain securely coupled to the cartridge 358 during a dispensing operation and will not release or otherwise move about.

The construction of the sheath 392 also provides various options for the dental practitioner in use. For example, the sheath 392 may be removed from the cartridge 358 and the static mixing assembly 366 while the cartridge 358 remains securely coupled to the applicator 310. Alternatively, the sheath 392 may remain in place over the cartridge 358 while the cartridge 358 is removed from the receptacle of the applicator 310.

Those skilled in the art can recognize that although a double barrel cartridge having two containers has been depicted in FIG. 17 for use with the hygienic sheath of the invention, a single barrel cartridge having only a single chamber may also be employed for use with the sheath. Also, while the discharge tip described with reference to FIG. 17 includes a static mixing element, a discharge tip without a static mixing element may also be used and may be preferred when a single barrel cartridge is provided.

An applicator 410 having a force limiting clutch constructed according to a presently preferred embodiment of the invention is illustrated in FIGS. 21–25. The applicator 410 is substantially identical to the applicator 210 described in connection with the embodiment shown in FIGS. 10–14 with the exception of the elements described below.

More particularly, the applicator 410 includes a housing 412 with a depending handle 414, an arm return spring (not shown in FIG. 21), and a clutch that are essentially the same as the housing 212, handle 214, spring 250 and the clutch respectively that are described above, and as such a detailed description need not be repeated.

Figure 21:
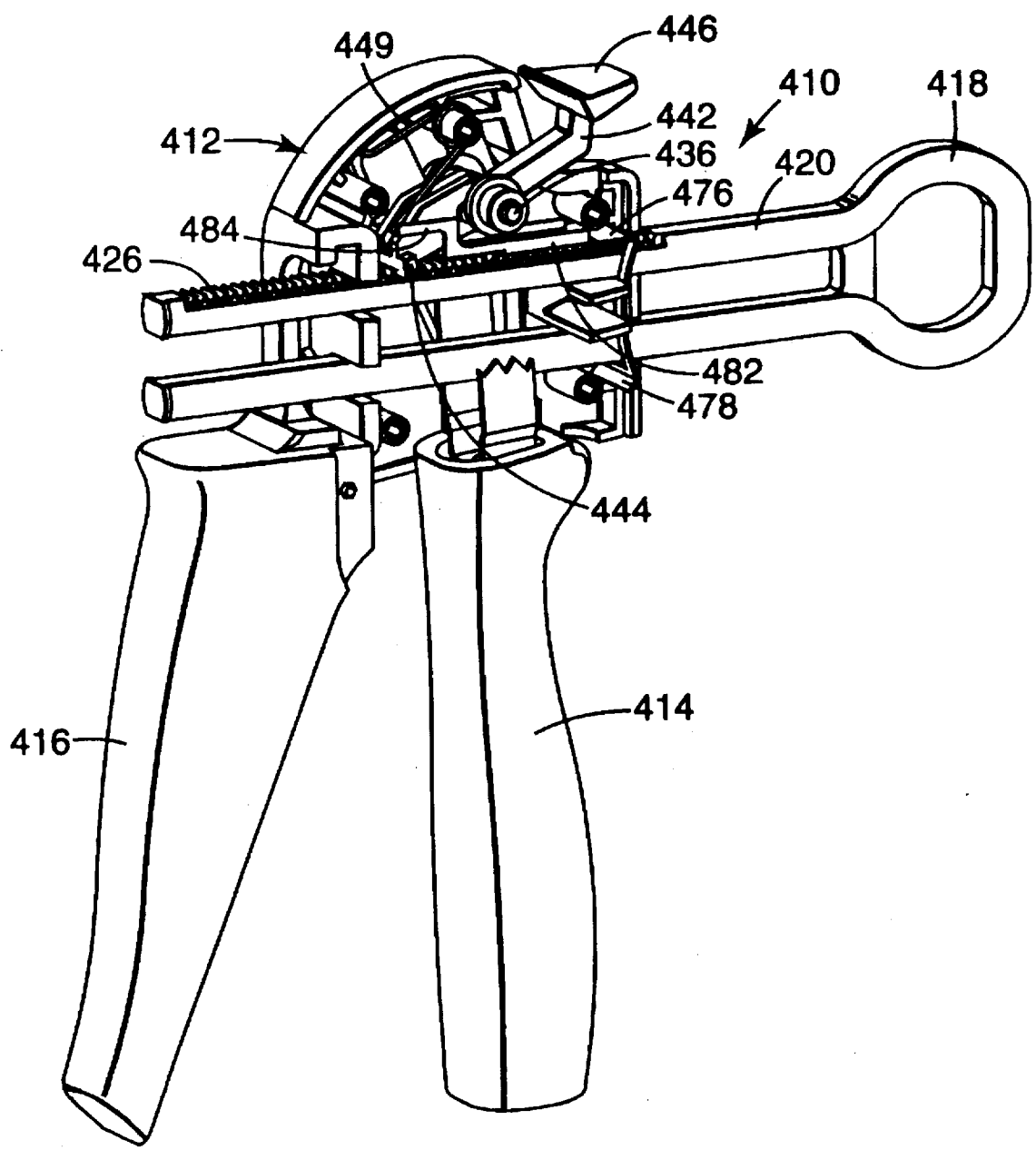
FIG. 21 is a perspective, fragmentary view of an applicator with parts broken away in section in accordance with another embodiment of the present invention, illustrating an integral pawl for hindering rearward movement of the plunger.
Figure 22:
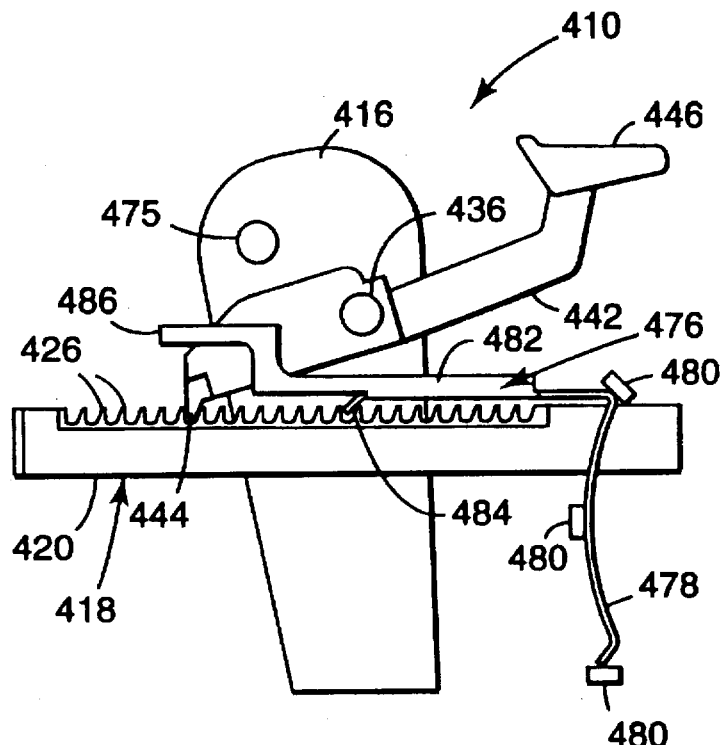
FIG. 22 is a schematic side elevational view of part of the applicator shown in FIG. 21.
Figure 23:
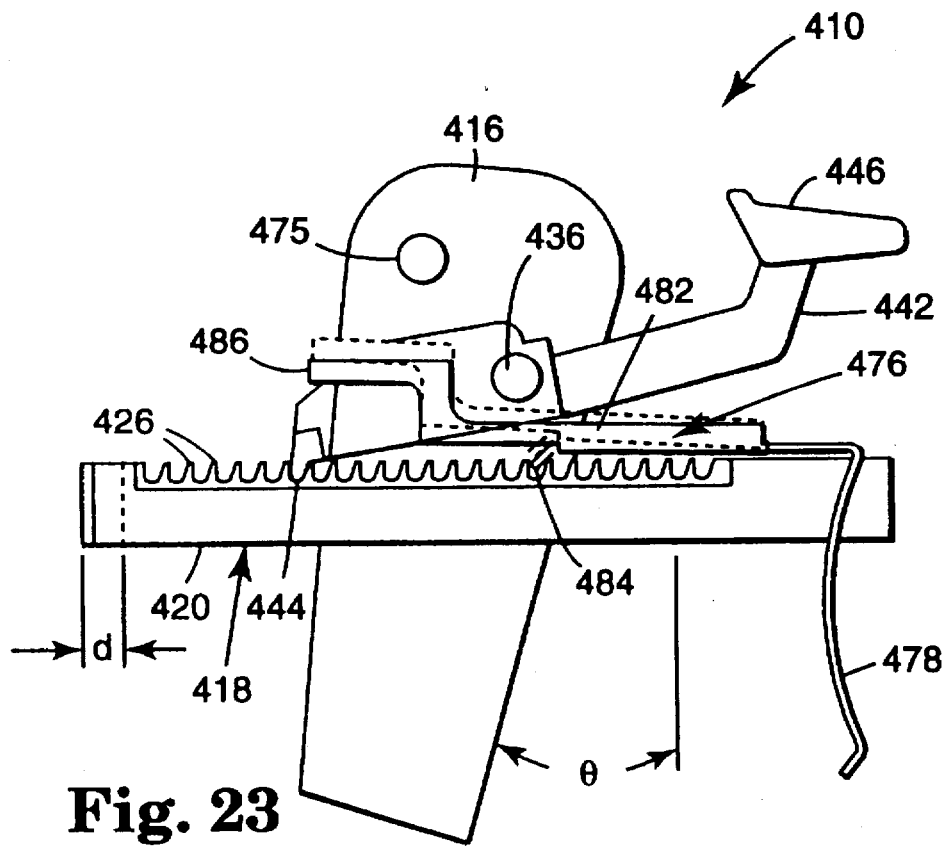
FIG. 23 is a view somewhat similar to FIG. 22 except that an arm of the applicator has been moved to advance the plunger.
Figure 24:
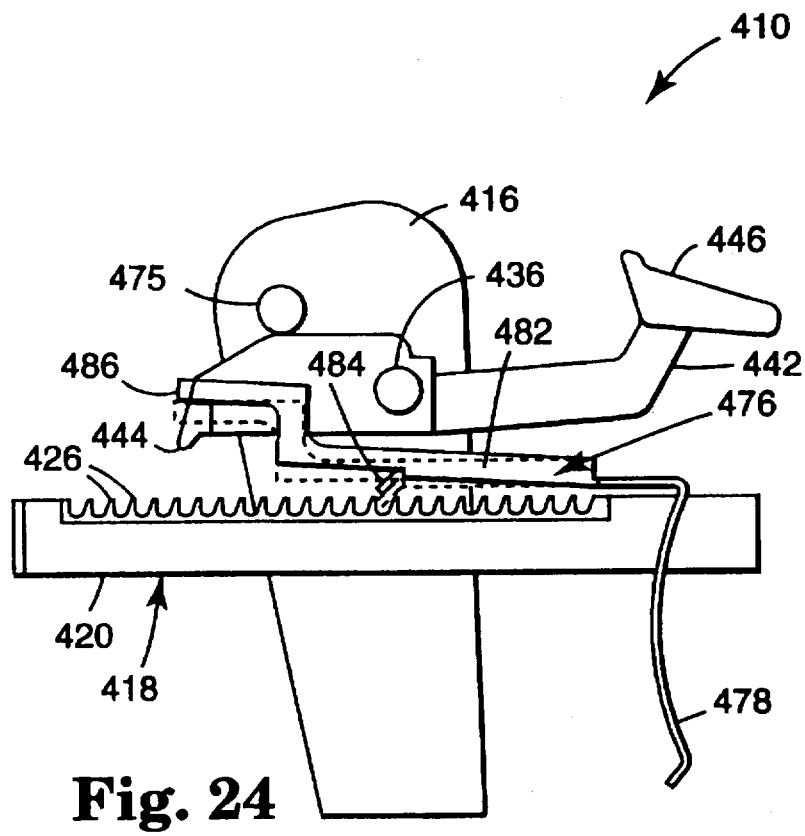
FIG. 24 is a view somewhat similar to FIG. 23 except that the pawl has been lifted from a row of rack teeth on the plunger in order to permit the user to retract the plunger.

An upper portion of an arm 416 of the applicator 410 bifurcated and in the drawings is shown only on one side. The arm 416 is shown for exemplary purposes in FIGS. 22–24 with a somewhat different configuration than its configuration as depicted in FIGS. 21, 25 and 10–14. However, it should be understood in this regard that the operation and function of the arms are essentially the same. In FIGS. 22–24, the arm 416 pivots relative to the housing about a pivot point 475, which if desired may be embodied by a pair of outwardly extending bosses similar to the bosses 275 illustrated in FIG. 12.

A ratchet mechanism of the applicator 410 includes a follower 442 that is pivotally connected to the arm 416 by a pin 436. A rear, upper portion of the follower 442 extends through an opening in the housing and terminates as a tab 446. A front portion of the follower 442 includes a chisel-shaped lower front edge 444 for engagement with an upper plunger rod 420 of a plunger 418 in the spaces between adjacent teeth of a row of rack teeth 426. The plunger 418 is essentially identical to the plunger 218 described above. As illustrated in FIG. 21, a torsion spring 449 urges the front edge 444 of the follower 442 into releasable engagement with the rack teeth 426. A lower portion of the torsion spring 449 bears against the bottom of a groove located on the top of the follower 442, and an upper portion of the spring 449 bears against an inner surface of a top section of the housing 412.

Figure 25:
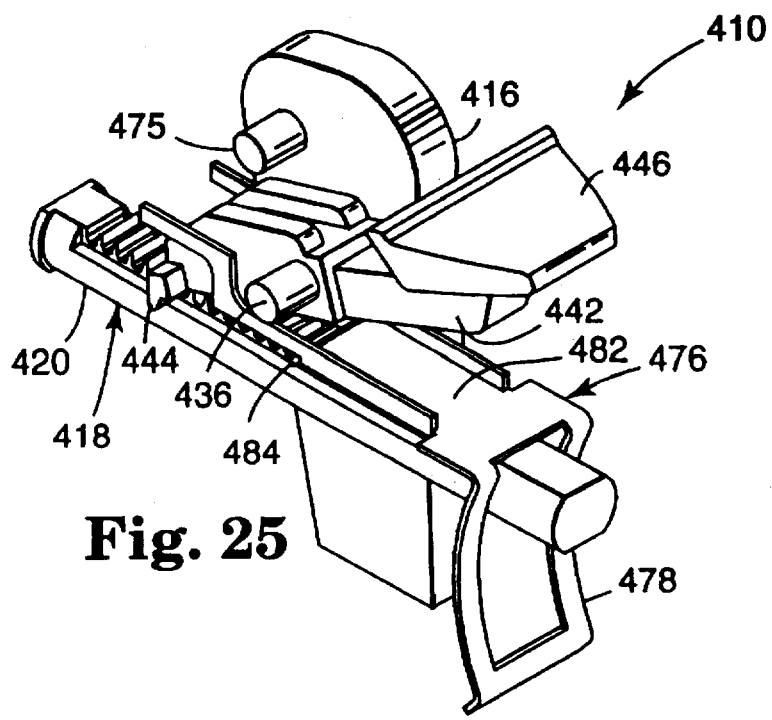
FIG. 25 is a perspective, fragmentary view of part of the applicator depicted in FIG. 21.

A pawl 476 is provided to hinder movement of the plunger in a rearward direction. The pawl 476 has a curved first section 478 that bears against a rear wall of the housing 412 next to holes in the housing 412 for passage of the rods of the plunger 418. As illustrated in FIGS. 21 and 25, the first section 478 has a rectangular opening that receives the upper plunger rod 420 as well as a lower plunger rod 422 (FIG. 21 only). In FIG. 22, the locations where the first section 478 bears against the housing 412 are designated by the rectangles numbered 480.

The pawl 476 includes a second section 482 that is integrally connected to the first section 478. The second section 482 includes a downwardly inclined portion or tooth 484 that is engagable with the row of rack teeth 426. Opposite side portions of the second section 482 are bent upwardly in parallel relation.

The pawl 476 also includes a third section 486 that extends outwardly from the second section 482. The third section 486 includes two segments that extend forwardly from the upstanding, parallel side portions of the second section 482. An outer or forward end of the third section 486 is offset and extends directly above the front edge 444. The front edge 444 extends in a transverse direction parallel to the grooves between adjacent rack teeth 426, and is longer than the distance between the two spaced apart segments of the overlying third section 486.

The first section 478, the second section 482 and the third section 486 are integral and made of a resilient material such as type 301 stainless steel. The pawl 476 has a configuration such that the tooth 484 is yieldably biased toward the rack teeth 426.

In use, the applicator 410 is grasped and the arm 416 is moved in a clockwise direction viewing FIG. 22. As a result, the front edge 444 bears against the rack teeth 426 and advances the plunger 418 in a forwardly direction. As the arm 416 moves from the orientation shown in FIG. 22 to the orientation shown in FIG. 23, the second and third section 482, 486 of the pawl 476 deflect and move upwardly a slight distance as indicated by the dashed lines in FIG. 23 such that the tooth 484 rides over the underlying rack teeth 426. Movement of the arm 416 from the orientation shown in FIG. 22 to the orientation shown in FIG. 23 through the arc designated "θ" in FIG. 23 advances the plunger 418 including the upper plunger rod 420 a distance that is represented by the letter "d".

When it is desired to retract the plunger 418 by pulling on the plunger 418 in a rearwardly direction, the user depresses the tab 446. Depression of the tab 446 pivots the follower 442 about the pin 436 in a clockwise direction viewing FIG. 24. As the follower 442 is pivoted in such a fashion, an upper wall of the front edge 444 engages the bottom of the outer front end of the third section 486 and raises the third section 486 along with the second section 482 from the dashed line orientation and to the full line orientation that is depicted in FIG. 24.

When the second section 482 is raised as shown in FIG. 24, the tooth 484 is lifted out of engagement with the rack teeth 426. As a consequence, rearward movement of the plunger 418 is now possible. Once the tab 446 is released, the torsion spring 449 returns the follower 442 to its orientation shown in FIG. 22, and the inherent resiliency of the pawl 476 causes the second section 482 and the third section 486 to return to their respective positions shown in FIG. 22 such that the tooth 484 re-engages the rack teeth 426.

The integral pawl 476 is an advantage in that it provides a compact construction that is especially useful for smaller applicators such as dental dispensers. Moreover, the pawl 476 is advantageous over the drag spring 252 shown in FIGS. 11 and 13–14, since the drag spring 252 applies friction to the plunger 218 when the plunger 218 is moving in the forward direction as well as in the rearward direction. Such friction not only increases the effort required to advance or retract the plunger 218, but also provides a certain amount of wear over a period of time.

While the foregoing paragraphs have set out a detailed description of the currently preferred embodiments, those skilled in the art can recognize that other modifications, additions and variations are possible without departing from the spirit of the invention. For example, while the drawings illustrate an applicator having a tooth and follower ratchet advancement mechanism, other types of advancement mechanisms (such as those used in many inexpensive, conventional caulking guns) may also be employed. Many other variations are also possible. As such, the scope of the invention should not be deemed limited by the preceding detailed description, but only by a fair reading of the claims that follow and their equivalents.

We claim:

1. A dispensing system comprising:
   an applicator having a body, an elongated handle connected to said body and a pair of plungers movable relative to said body;
   a first container connected to said body and having a chamber with a longitudinal axis;
   a second container connected to said body and having a chamber with a longitudinal axis; and
   an arm pivotally coupled to said body and movable relative to said handle for moving said plungers,
   said plungers being movable toward said chambers of said first container and said second container, said axes of said first container and said second container generally lying in a common reference plane, said handle depending from said body in a direction generally parallel to said reference plane, said chambers of said first container and said second container each having a component of a dental material.

2. The dispensing system of claim 1, wherein said first container is integrally connected with said second container.

3. The dispensing system of claim 1, wherein said dispensing system includes an exit conduit and a static mixing element located in said exit conduit, said exit conduit being connected to said first container and said second container.

4. The dispensing system of claim 3, wherein said exit conduit and said static mixing element are elongated and curved in a direction along their longitudinal axes.

5. The dispensing system of claim 3, wherein said dispensing system includes a cannula connected to said exit conduit.

6. The dispensing system of claim 5, wherein said cannula is elongated and curved in a direction along its longitudinal axis.

7. The dispensing system of claim 5, wherein said cannula is elongated and swivelable in directions about its longitudinal axis relative to said exit conduit.

8. The dispensing system of claim 1, wherein said first container and said second container each have a rear opening that is located rearwardly of said handle.

9. The dispensing system of claim 1, wherein said plungers have parallel longitudinal axes, and wherein said handle extends at an angle of less than about 90 degrees relative to said longitudinal axes of said plungers.

10. A dispensing system comprising:
    an applicator having a body, an elongated handle connected to said body and a pair of plungers movable relative to said body;
    a first container connected to said body and having a chamber with a longitudinal axis;
    a second container connected to said body and having a chamber with a longitudinal axis,
    said plungers being movable toward said chambers of said first container and said second container, said axes of said first container and said second container generally lying in a common reference plane, said handle depending from said body in a direction generally parallel to said reference plane, said chambers of said first container and said second container each having a component of a dental material,
    wherein said system includes a flange connected to said first container and said second container, wherein said applicator includes a receptacle for receiving said flange and a tab extending into said receptacle, and wherein said flange includes a recess that receives said tab when said flange is received in said receptacle.

11. The dispensing system of claim 10, wherein said applicator includes an arm coupled to said body and movable relative to said handle for moving said plungers, and wherein said handle and said arm have generally equal lengths.

12. The dispensing system of claim 10, wherein said applicator includes a coil spring for urging said arm away from said handle, said spring surrounding one of said plungers.

13. The dispensing system of claim 10, wherein said first container and said second container include a forward outlet, and wherein said arm is located rearwardly of said handle and said forward outlet of said first container and said second container.

14. The dispensing system of claim 10, wherein said first container and said second container each have a rear opening that is located rearwardly of said handle and forwardly of said arm.

15. The dispensing system of claim 10, wherein said applicator includes a pivot coupling said arm to said body, and wherein said plungers are located between said pivot and said arm.

16. A method of dispensing dental material made of a first and second component to a location in the oral cavity of a patient comprising the steps of:

providing a first and second container each having an elongated chamber containing a component of a dental material;

connecting the first and second containers to a dispensing applicator having a depending handle;

holding the applicator in an orientation wherein the handle is generally parallel to the occlusal plane of the patient; and simultaneously orienting the longitudinal axes of the chambers of the first and second containers in a side-by-side, mesial and distal relationship to each other relative to mesial and distal directions in the patient's oral cavity as the first and second component are dispensed toward a location in the oral cavity.

17. The method of claim 16, including the step of directing the first and second component through an exit conduit containing a static mixing element.

18. The method of claim 17, including the step of passing the first and second component through a cannula connected to the exit conduit downstream of the static mixing element.

19. The method of claim 16, including the step of moving an arm of the applicator in a forward direction toward the oral cavity in order to dispense the first and second component.

20. The method of claim 19, wherein said step of moving the arm includes the step of pivoting the arm about an axis located above the first and second container.

21. The method of claim 19, wherein said step of orienting the longitudinal axes of the chambers includes the step of orienting the longitudinal axes of the chambers in a common plane generally parallel to the occlusal plane of the patient.

22. An applicator for dispensing material from a cartridge having a first chamber and a second chamber in side-by-side relation to said first chamber, said applicator comprising:

a body;

a handle depending from said body;

an arm located next to said handle and movable relative to said body;

a first elongated plunger movably connected to said body;

a second elongated plunger coupled to said first plunger in side-by-side relation and movably connected to said body, said arm when moved relative to said body being operable to move said first plunger and said second plunger in a forwardly direction relative to said body; and a pivot connecting said arm to said body, said first plunger and said second plunger being located between said pivot and said arm, wherein said body includes a receptacle for receiving a flange of a cartridge, and wherein said receptacle is located rearwardly of said handle.

23. The applicator of claim 22, wherein the longitudinal axes of said first plunger and said second plunger lie in a common reference plane, and wherein said handle has a longitudinal axis that is generally parallel to said reference plane.

24. The applicator of claim 23, wherein said applicator includes a pawl next to said pivot, and wherein one of said plungers includes a series of teeth engagable with said pawl as said plungers are moved in the forwardly direction.

25. The applicator of claim 22, wherein said applicator includes a coil spring for urging said arm away from said handle, and wherein said coil spring surrounds one of said plungers.

26. The applicator of claim 22, wherein said handle and said arm have generally equal lengths.

27. An applicator for dispensing material from a cartridge having a first chamber and a second chamber in side-by-side relation to said first chamber, said applicator comprising:

a body;

a handle depending from said body;

an arm located next to said handle and movable relative to said body;

a first elongated plunger movably connected to said body;

a second elongated plunger coupled to said first plunger in side-by-side relation and movably connected to said body, said arm when moved relative to said body being operable to move said first plunger and said second plunger in a forwardly direction relative to said body; and a pivot connecting said arm to said body, said first plunger and said second plunger being located between said pivot and said arm, wherein said body includes a receptacle for receiving a flange of a cartridge, and wherein said applicator includes a tab extending into said receptacle for engaging a recess in the flange of the cartridge.

28. An applicator for dispensing material from a cartridge having a first chamber and a second chamber in side-by-side relation to said first chamber, said applicator comprising:

a body;

a handle depending from said body;

an arm located next to said handle and movable relative to said body;

a first elongated plunger movably connected to said body;

a second elongated plunger coupled to said first plunger in side-by-side relation and movably connected to said body, said arm when moved relative to said body being operable to move said first plunger and said second plunger in a forwardly direction relative to said body;

a pivot connecting said arm to said body, said first plunger and said second plunger being located between said pivot and said arm, wherein said handle is located forwardly of said arm, wherein said body includes a receptacle for receiving a flange of a cartridge, and wherein said receptacle is located rearwardly of said handle.

29. A dispensing system comprising:

an applicator having a body with a receptacle, a handle connected to the body and a pair of plungers movable relative to the body; and a cartridge having a first container, a second container and a flange connected to said first container and said second container, said first container and said second container each including a chamber containing one component of a material to be dispensed, said flange being detachably received in said receptacle for connecting said cartridge to said body, said plungers being movable in respective chambers to dispense the component in each chamber, one of said flange and said receptacle including a recess, the other of said flange and said receptacle including a tab received in said recess when said flange is received in said receptacle.

30. The system of claim 29, wherein said tab is connected to said receptacle and has a generally U-shaped configuration.

31. The system of claim 29, wherein said flange includes said recess and wherein said recess has a generally U-shaped configuration.

32. The system of claim 29, wherein said flange has a side and includes said recess, and wherein said recess extends partially along said side.

33. The system of claim 29, wherein said first container and said second container each include a rear opening surrounded by said flange, wherein said flange has a side, a rear end and includes said recess, and wherein said recess extends partially along said side and said end directly adjacent said rear opening of one of said containers.

34. A dispensing cartridge comprising:
a first container having a chamber with a rear opening;
a second container having a chamber with a rear opening; and
a flange connected to said first container and said second container and surrounding said rear opening of said first container and said second container, said flange including an outer side and a rear end, said flange including at least one recess extending at least partially along said side and said end.

35. The dispensing cartridge of claim 34, wherein each recess is directly adjacent one of said rear openings.

36. The dispensing cartridge of claim 34, wherein said chambers have parallel longitudinal axes, and wherein each recess has a generally U-shaped configuration in a reference plane perpendicular to said longitudinal axes.

37. The dispensing cartridge of claim 34, wherein said chambers each have a central longitudinal axis parallel to one another, and wherein each recess extends inwardly toward said central axis of one of said chambers.

38. A dispensing system comprising:
an applicator having a body with a receptacle and a plunger movably connected to said body;
a container removably received in said receptacle and including a chamber for containing a material to be dispensed, said plunger being movable toward said chamber in order to dispense material from said chamber;
a discharge tip detachably connected to said container for conveying material dispensed from said container toward an application site, said discharge tip including a section being made of a material having a certain Young's modulus; and
a hygienic sheath extending over at least a portion of said container and said discharge tip, said sheath including a portion that is in interference fit relation with said section of said discharge tip for releasably retaining said sheath in coupled relation to said discharge tip, said sheath portion being made of a relatively rigid material having a higher Young's modulus than said certain Young's modulus of said material of said discharge tip section.

39. The dispensing system of claim 38, wherein said discharge tip includes a static mixing element.

40. The dispensing system of claim 38, and including a second container for containing a material to be dispensed.

41. The dispensing system of claim 38, wherein said discharge tip includes a bendable cannula.

42. The dispensing system of claim 38, wherein said discharge tip and said container include a coupling for connecting said discharge tip to said container, said coupling being shiftable between a locked orientation wherein said discharge tip is non-releasably connected to said container and an unlocked orientation wherein said discharge tip may be released from said container, and wherein said sheath when extending over said at least a portion of said container and said discharge tip retains said coupling in said locked orientation.

43. A dispensing system comprising:
an applicator having a body with a receptacle and a plunger movably connected to said body;
a container removably received in said receptacle and including a chamber for containing a material to be dispensed, said plunger being movable toward said chamber in order to dispense material from said chamber;
a discharge tip for conveying material dispensed from said container toward an application site;
a coupling for connecting said discharge tip to said container, said coupling being shiftable between a locked orientation wherein said discharge tip is non-releasably connected to said container and an unlocked orientation wherein said discharge tip may be released from said container; and
a hygienic sheath removably extending over at least a portion of said container and said discharge tip, said sheath when extending over said at least a portion of said container and said discharge tip retaining said coupling in said locked orientation.

44. The dispensing system of claim 43, wherein said coupling comprises a flange of said discharge tip and ears of said container, and wherein said flange and said ears form a bayonet-type coupling.

45. The dispensing system of claim 43, and including a second container removably received in said receptacle.

46. The dispensing system of claim 43, wherein said discharge tip includes at least one rib, and wherein said sheath includes an opening having a slot that receives said rib.

* * * * *